(12) United States Patent
El Shami et al.

(10) Patent No.: US 7,833,729 B2
(45) Date of Patent: Nov. 16, 2010

(54) METHOD FOR DETECTING ENDOMETRIOSIS IN A PATIENT SAMPLE

(75) Inventors: A. Said El Shami, Camarillo, CA (US); Surendra Nath Menon, Culver City, CA (US); Cynthia K. French, Irvine, CA (US)

(73) Assignee: Siemens Heathcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 12/586,527

(22) Filed: Sep. 22, 2009

(65) Prior Publication Data

US 2010/0086940 A1 Apr. 8, 2010

Related U.S. Application Data

(60) Continuation of application No. 11/168,187, filed on Jun. 27, 2005, now abandoned, which is a division of application No. 10/172,573, filed on Jun. 13, 2002, now Pat. No. 7,368,533, which is a division of application No. 09/447,399, filed on Nov. 23, 1999, now Pat. No. 6,525,187, which is a continuation-in-part of application No. 09/359,084, filed on Jul. 22, 1999, now abandoned.

(60) Provisional application No. 60/094,930, filed on Jul. 31, 1998.

(51) Int. Cl.
*G01N 33/53* (2006.01)

(52) U.S. Cl. .................. 435/7.1; 435/7.92; 436/506

(58) Field of Classification Search ........................ None
See application file for complete search history.

(56) References Cited

U.S. PATENT DOCUMENTS 5,539,082 A 7/1996 Nielsen et al.
5,650,297 A 7/1997 Takahashi et al.
5,872,235 A 2/1999 Chen et al.
5,880,261 A 3/1999 Waeber et al.

FOREIGN PATENT DOCUMENTS

WO WO 94/82021 A1 12/1994

OTHER PUBLICATIONS

The Merck Manual of Diagnosis and Therapy, 17 edition, 1999, Merck Research laboratories, pp. 1956-1959.*
Colman, PM, Research in Immunology, 1994, 145:33-36.*
Emest24 Database Entry Hs888330 Accession No. W19888: May 5, 1996 Hillier, et. al.: "The Wash-U-Merck EST Project" XP002126944 "the whole document".
EMBL Database Entry A1832097 Accession No. A1832097: Jul. 13, 1999 Robert Strausberg XP002141979 "the whole document".
GenBank Accession No. G05536.1 GI:858781, (GenBank (Oct. 19, 1995) pp. 1-2).
Cheung, et. al., "Natural variation in human gene expression assessed in lymphoblastoid cells", Nature Genetics, 33:422-425 (2003).
Colman, "Effects of amino acid sequence changes on antibody-antigen interactions", Research in Immunology, 145(1):33-36 (1994).
Dermer, "Another Anniversary for the War on Cancer", Bio/Technology, 12:320 (Mar. 12, 1994).
Ogawa, et. al., "Ovarian Endometriosis Associated with Ovarian Carcinoma: A Clinicopathological and Immunohistochemical Study", Gynecological Oncology, 77:298-304 (2000).
Van Regenmortel, Methods: A Companion to Methods in Enzymology, 9:465-472 (1966).

* cited by examiner

*Primary Examiner*—Michael Szperka
(74) *Attorney, Agent, or Firm*—Kevin Stein

(57) ABSTRACT

This invention provides a polynucleotide encoding Repro-EN-1.0 and IB1, polypeptides associated with endometriosis. Auto-antibodies against Repro-EN-1.0 and IB1 have been found in subjects diagnosed with endometriosis. This invention also provides methods of using this polynucleotide and polypeptide.

9 Claims, 3 Drawing Sheets

METHOD FOR DETECTING ENDOMETRIOSIS IN A PATIENT SAMPLE

CROSS-REFERENCE TO RELATED APPLICATION

This application is related to co-pending application of Schneider et al., "Diagnosis Of Autoimmune Disease By Detecting IgE or IgG$_4$, Autoantibodies Against Autoantigens," filed on even date herewith, the content of which is incorporated herein by reference in its entirety.

This application is a continuation of U.S. patent application Ser. No. 11/168,187 filed Jun. 27 2005 now abandoned which is a divisional of U.S. patent application Ser. No. 10/172,573 filed Jun. 13, 2002, and issued as U.S. Pat. No. 7,368,533, which, in turn, is a divisional of U.S. patent application Ser. No. 09/447,399, filed Nov. 23, 1999, and issued as U.S. Pat. No. 6,525,187, which in turn is a continuation in part of U.S. patent application Ser. No. 09/359,084 filed Jul. 22, 1999, now abandoned which, in turn, is a continuation of Provisional Patent Application Ser. No. 60/094,930, filed Jul. 31, 1998, all of which are incorporated herein by reference in their entirety.

FEDERALLY SPONSORED RESEARCH OR DEVELOPMENT

Certain work described herein was supported by SBIR grant no. 1R43 HD 33022-01A2 between the United States Department of Health and Human Services and Reprogen, Inc. The Government may have certain rights in this invention.

FIELD OF THE INVENTION

This invention is directed to the field of molecular biology in general, and, more specifically, to a polypeptide associated with endometriosis, an isolated polynucleotide encoding the polypeptide, and methods of using these molecules.

BACKGROUND OF THE INVENTION

Endometriosis is a painful disorder that is characterized by the ectopic implantation of functioning endometrial tissue into the abdominal wall and the outer surface of various organs including, most commonly, the lower bowel, ovaries and fallopian tubes. P. Vigano et al. (1991) *Fertility and Sterility* 56:894. Currently, endometriosis-specific genes have not been identified and the events relating to the development of endometriosis are poorly understood. However, several reports suggest that retrograde menstruation linked with abnormal immune function may play a role in establishing ectopic endometrium lesions. T. Ishimaru and H. Masuzaki (1991) *Am. J. Obstet. Gynecol.* 165:210-214. Many attempts to isolate antigens from ectopic endometrium lesions have failed, due to the necrotic nature of the lesions.

Endometriosis also is recognized has having an autoimmune component. IgG and IgA auto-antibodies that react with multiple endometrial antigens have been documented in patients with endometriosis. However, attempts to develop IgG or IgA-based assays for the diagnosis of endometriosis has fallen short of fruition. S. Fernandez-Shaw et al., (1996) *Hum. Reprod.* 11:180-1184. R. A. Wild et al. (1991) *Obstetrics and Gynecology* 77:927. Studies have shown that circulating IgG antibodies that bind multiple endometrial proteins can be detected in women with endometriosis to varying degrees. Thirty-five percent to 74% of patients have sera reactive with endometrial proteins. O. Odukoya et al. (1996) *Acta Obstet. Gynecol. Scand.* 75:927-931; J. G. Kim et al. (1995) *Am. J. Reprod. Immunol.* 34:80-87; O. A. Odukoya et al. (1995) *Hum. Reprod.* 10:1214-1219. It has also been shown that endometrial antibody titers in patients that respond well to danazol are significantly lower (7/18 (39%) treated patients had elevated titers) than those patients with untreated endometriosis or patients that responded poorly to treatment (17/23 (74%) untreated patients had elevated titers). A. El-Roeiy et al. (1988) *Fertility and Sterility* 50:864-871; H. J. Chihal et al. (1986) *Fertility and Sterility* 46:408-411. In addition, it has been recently reported that women with endometriosis have elevated levels of IL-4, a Th2 mediating cytokine, and that treatment with danazol reduces the levels of IL-4 in women that respond well to treatment. C.-C. Hsu et al. (1997) *Fertility and Sterility* 67:1059-1064.

SUMMARY OF THE INVENTION

This invention provides an isolated cDNA molecule and an alternately spliced variant encoding autoantigens associated with endometriosis. The autoantigen is called Repro-EN-1.0. The alternately spliced variant is called IB1. Subjects diagnosed with endometriosis have been found to have antibodies that specifically bind to Repro-EN-1.0 polypeptide and/or a IB1 polypeptide. These antibodies represent a highly sensitive and specific diagnostic marker for endometriosis. Recombinant Repro-EN-1.0 protein and recombinant IB1 protein are useful to detect such antibodies in immunoassays.

In one aspect this invention provides a recombinant polynucleotide comprising a nucleotide sequence encoding a polypeptide epitope of at least 5 amino acids of Repro-EN-1.0 (SEQ ID NO:2), or IB1 (SEQ ID NO:4) wherein the epitope specifically binds to antibodies from subjects diagnosed with endometriosis. In one embodiment the nucleotide sequence is selected from the Repro-EN-1.0 sequence of SEQ ID NO:1 or IB1 sequence of SEQ ID NO: 3. In another embodiment the nucleotide sequence is identical to nucleotides 176 to 2755 of SEQ ID NO:1 or nucleotides 176 to 2986 of SEQ ID NO:3. In another embodiment the polynucleotide further comprises an expression control sequence operatively linked to the nucleotide sequence.

In another aspect this invention provides a polynucleotide primer pair which amplifies a nucleotide sequence encoding a polypeptide epitope of at least 5 amino acids of Repro-EN-1.0, or IB1 wherein the epitope specifically binds to antibodies from subjects diagnosed with endometriosis. The pair comprises: 1) a 3' primer of at least 7 nucleotides that specifically hybridizes to a 3' end of the nucleotide sequence or downstream from the sequence, and 2) a 5' primer of at least 7 nucleotides that specifically hybridizes to the 3' end of the complement of the nucleotide sequence or downstream from the complement of the sequence.

In another aspect this invention provides a recombinant cell comprising a recombinant polynucleotide comprising an expression control sequence operatively linked to a nucleotide sequence encoding a polypeptide epitope of at least 5 amino acids of Repro-EN-1.0 (SEQ ID NO:2), or IB1 (SEQ ID NO:4), wherein the epitope specifically binds to antibodies from subjects diagnosed with endometriosis.

In another aspect this invention provides a method for detecting a target polynucleotide comprising a nucleotide sequence selected from Repro-EN-1.0 cDNA (SEQ ID NO: 1) or its complement, or IB1 cDNA (SEQ ID NO:3) or its complement in a sample. The method comprises the steps of: (a) contacting the sample with a polynucleotide probe or primer comprising a sequence of at least 7 nucleotides that specifically hybridizes to the nucleotide sequence and (b) detecting whether the probe or primer has specifically hybridized to the target polynucleotide, whereby specific hybridization provides a detection of the target polynucleotide in the sample.

In another aspect this invention provides a purified, recombinant Repro-EN-1.0 polypeptide whose amino acid sequence is identical to that of SEQ ID NO:2, or an allelic variant of SEQ ID NO:2, or an IB1 polypeptide whose amino acid sequence is identical to that of SEQ ID No:4, or an allelic variant of SEQ ID: No:4.

In another aspect this invention provides a purified polypeptide comprising an epitope of at least 5 amino acids of Repro-EN-1.0 (SEQ ID NO:2), or an epitope of at least 5 amino acids of IB1 (SEQ ID NO:4), wherein the epitope specifically binds to antibodies from subjects diagnosed with endometriosis.

In another aspect this invention provides a composition consisting essentially of an antibody that specifically binds to Repro-EN-1.0 polypeptide (SEQ ID NO: 2), or IB1 polypeptide (SEQ ID NO:4).

In another aspect this invention provides a method for detecting a Repro-EN-1.0 polypeptide or IB1 polypeptide in a sample. The method comprises the steps of: (a) contacting the sample with a ligand that specifically binds to the Repro-EN-1.0 polypeptide or IB1 polypeptide and (b) detecting specific binding between the ligand and Repro-EN-1.0 polypeptide or IB1 polypeptide. Specific binding provides a detection of Repro-EN-1.0 polypeptide or IB1 polypeptide in the sample. In one embodiment, the ligand is an antibody.

In another aspect this invention provides a method diagnosing endometriosis in a subject. The method comprises the steps of: (a) detecting a test amount of an antibody that specifically binds to Repro-EN-1.0 polypeptide or IB1 polypeptide in a sample from the subject; and (b) comparing the test amount with a normal range of the antibody in a control sample from a subject who does not suffer from endometriosis. A test amount above the normal range provides a positive indication in the diagnosis of endometriosis. The sample can be a blood product, e.g., serum, peritoneal fluid, menstrual fluid, vaginal secretion or urine. In one embodiment the antibody is an IgE, IgG or $IgG_4$ immunoglobulin. In another embodiment the step of detecting comprises capturing the antibody from the sample with an immobilized Repro-EN-1.0 or a peptide comprising an epitope of Repro-EN-1.0 or IB1 or a peptide comprising an epitope of IB1, and detecting captured antibody. The step of detecting captured antibody can comprise contacting the captured antibody with a detectable antibody that specifically binds immunoglobulins and detecting binding between the captured antibody and the detectable antibody. In another embodiment the step of detecting can comprise capturing the antibody from the sample with an immobilized anti-immunoglobulin antibody and detecting captured antibody. The step of detecting captured antibody can comprise contacting the captured antibody with Repro-EN-1.0 or a polypeptide, or IB1 or a peptide comprising an epitope of IB1, comprising an epitope of Repro-EN-1.0 and detecting binding between the captured antibody and the Repro-EN-1.0 or polypeptide or IB1 or polypeptide.

In another aspect this invention provides a method for use in following the progress of endometriosis in a subject. The method comprises the steps of: (a) detecting first and second amounts of an antibody that specifically bind Repro-EN-1.0 polypeptide, or IB1 polypeptide, in samples from the subject at a first and a second time, respectively; and (b) comparing the first and second amounts. An increase between the first and second amounts indicates progression of the endometriosis and a decrease between the first and second amounts indicates remission of the endometriosis.

In another aspect this invention provides an isolated MHC-peptide complex comprising at least a portion of an MHC Class I molecule or an MHC Class II molecule, wherein the portion comprises a binding site that specifically binds a peptide having an amino acid binding motif specific to the molecule, and wherein the portion engages in CD4-mediated or CD8-mediated binding to T cells, and a peptide of at least 8 amino acids in a sequence selected from the amino acid sequence of Repro-EN-1.0 (SEQ ID NO:2) or IB1 (SEQ ID NO:4), wherein the peptide comprises the amino acid binding motif and comprises an epitope that specifically binds to a T cell receptor; wherein the complex specifically binds a T cell having a T cell receptor that specifically binds to the epitope, and wherein specific binding induces anergy in the T cell.

In another aspect this invention provides a method for treating endometriosis in a subject comprising the step of inhibiting an immune response against Repro-EN-1.0 or IB1 in the subject. The method can comprise administering to the subject an immunosuppressant in an amount effective to inhibit the immune response, administering to the subject an isolated MHC-peptide complex of the invention in an amount effective to inhibit the immune response or administering to the subject an anti-idiotypic antibody that specifically binds to an antigen binding site of an antibody that specifically binds to Repro-EN-1.0 or IB1 in an amount effective to inhibit the immune response.

In another aspect this invention provides a screening method for determining whether a compound increases or decreases the expression of Repro-EN-1.0 in a cell comprising contacting the cell with the compound and determining whether the production of Repro-EN-1.0 mRNA or polypeptide, or IB1 mRNA or polypeptide, are increased or decreased.

In another aspect this invention provides a method of detecting a chromosomal translocation of a Repro-EN-1.0 gene or IB1 gene comprising the steps of: a) hybridizing a labeled polynucleotide probe that specifically hybridizes with the Repro-EN-1.0 nucleotide sequence of SEQ ID NO:1 or its complement, or IB1 nucleotide sequence of SEQ ID NO:3 or its compliment, to a chromosome spread from a cell sample to determine the pattern of hybridization and b) determining whether the pattern of hybridization differs from a normal pattern. A difference in the pattern provides detection of a translocation.

In another aspect this invention provides a method of detecting polymorphic forms of Repro-EN-1.0 or IB1 comprising the steps of: a) determining the identity of a nucleotide or amino acid at a selected position within the sequence of a test Repro-EN-1.0 gene or polypeptide, IB1 gene or polypeptide; b) determining the identity of the nucleotide or amino acid at the corresponding position of native Repro-EN-1.0 (SEQ ID NO: 1 or 2) gene or polypeptide, or IB1 (SEQ No:3 or 4) gene or polypeptide; and c) comparing the identity from the test gene or polynucleotide with the identity of the native gene or polypeptide, whereby a difference in identity indicates that the test polynucleotide is a polymorphic form of Repro-EN-1.0 or IB1.

DETAILED DESCRIPTION OF THE INVENTION

I Definitions

Figure 1:
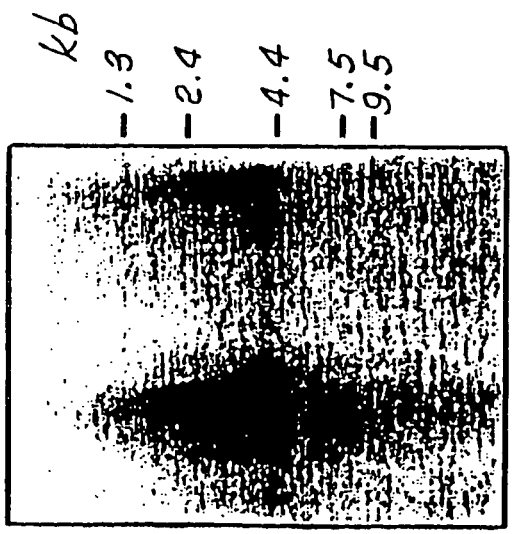
FIG. 1 is a northern blot analysis of Repro-EN-1.0 expression in various tissues.
Figure 1:
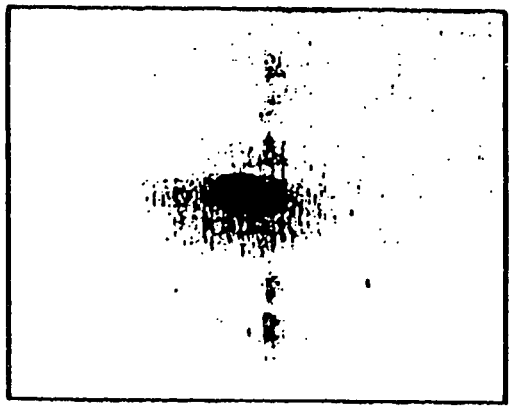
Figure 1:

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the con-tact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology Hybridization with Nucleic Acid Probes* part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

The terms "identical" or percent "identity," in the context of two or more polynucleotide or polypeptide sequences, refer to two or more sequences or sub-sequences that are the same or have a specified percentage of nucleotides or amino acid residues that are the same, when compared and aligned for maximum correspondence, as measured using one of the following sequence comparison algorithms or by visual inspection.

The phrase "substantially identical," in the context of two nucleic acids or polypeptides, refers to two or more sequences or sub-sequences that have at least 60%, 80%, 90%, 95% or 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word-length (W) of 11, an expectation (E) of 10, M=5, N=−4, and a comparison of both strands. For amino acid sequences, the BLASTP program uses as defaults a word-length (W) of 3, an expectation (E) of 10, and the BLOSUM62 scoring matrix (see Henikoff & Henikoff, *Proc. Natl. Acad. Sci.* USA 89:10915 (1989)).

In addition to calculating percent sequence identity, the BLAST algorithm also performs a statistical analysis of the similarity between two sequences (see, e.g., Karlin & Altschul, Proc. *Proc. Natl. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

An "affinity agent" is a compound that specifically or non-specifically binds to a target molecule. Affinity agents that non-specifically bind to a molecule include, for example, anion or cation exchange resins, or materials that bind hydrophobic or hydrophilic molecules, or metal ions.

A "ligand" is a compound that specifically binds to a target molecule.

A "receptor" is compound that specifically binds to a ligand.

"Antibody" refers to a polypeptide ligand substantially encoded by an immunoglobulin gene or inimunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, CH, CH2 and CH3, but does not include the heavy chain variable region.

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

"Immunoassay" refers to a method of detecting an analyte in a sample in which specificity for the analyte is conferred by the specific binding between an antibody and a ligand. This includes detecting an antibody analyte through specific binding between the antibody and a ligand. See Harlow and Lane (1988) *Antibodies, A Laboratory Manual*, Cold Spring Harbor Publications, New York, for a description of immunoassay formats and conditions that can be used to determine specific immunoreactivity.

"Vaccine" refers to an agent or composition containing an agent effective to confer a therapeutic degree of immunity on an organism while causing only very low levels of morbidity or mortality. Methods of making vaccines are, of course, useful in the study of the immune system and in preventing and treating animal or human disease.

An "immunogenic amount" is an amount effective to elicit an immune response in a subject.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, *Bio/Technology* (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis or treatment is a human or non-human mammal. Non-human mammals subject to diagnosis or treatment include, for example, primates, ungulates, canines and felines.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

"Prognostic" means predicting the probable development (e.g., severity) of a pathologic condition.

"Test amount" refers to an amount of an analyte in a subject sample, which is then compared to a normal amount of the analyte in a sample (e.g., from a healthy individual) such that the relative comparison of the values provides a reference value for diagnosing a designated disease. Depending upon the method of detection, the test amount may be a determination of the amount of the analyte, but it is not necessarily an amount. The test amount may also be a relative value, such as a plus or a minus score, and also includes an amount indicating the presence or absence of the analyte in a sample.

"Normal amount" refers to an amount or a range of an analyte in a biological sample that indicates health or lack of pathology.

"Diagnostic amount" refers to an amount of an analyte in a subject sample that is consistent with a particular diagnosis for a designated disease.

"Prognostic amount" refers to an amount or range of an analyte in a subject sample that is consistent with a particular prognosis for a designated disease.

"Plurality" means at least two.

An "epitope" is portion of a molecule that specifically binds to an antibody or a T cell receptor. An peptide epitope generally comprises a sequence of at least 6 amino acids from a polypeptide, although longer and shorter peptides can constitute epitopes.

"MHC Class I molecule" refers to a heterodimer found on the surface of cells that present processed antigenic peptides to T cells. The molecule comprises an α chain and a β-microglobulin chain. The α chain contains the antigenic peptide binding site in the α1 and α2 domains. The α chain also contains a transmembrane portion that can be removed without eliminating antigen binding.

"MHC Class II molecule" refers to a heterodimer found on the surface of cells that present processed antigenic peptide to T cells. It comprises an α chain and a β chain. The antigenic peptide binding site is located in the α1 domain of the α chain and the β1 domain of the β chain. However, a single a chain or β chain suffices to bind an antigenic peptide. The α chain and β chain also contain transmembrane regions that can be removed without eliminating antigenic peptide binding function.

"T cell receptor" refers to a heterodimer found on the surface of T cells comprising an α chain and a β chain or a γ and a δ chain. T cell receptors recognize processed antigens associated with MHC molecules.

II cDNA Encoding Repro-EN-1.0 and IB1

We have isolated a cDNA molecule encoding an autoantigen associated with endometriosis. The autoantigen is called Repro-EN-1.0. The presence of antibodies that specifically bind to an epitope of the Repro-EN-1.0 polypeptide is a highly sensitive and specific diagnostic marker for endometriosis.

Polynucleotides encoding full-length Repro-EN-1.0 are useful in recombinant production Repro-EN-1.0 or immunogenic fragments of it. Fragments of polynucleotides encoding Repro-EN-1.0 are useful as probes to detect Repro-EN-1.0 mRNA from certain cell types suspected to be cancerous. Fragments also are useful as primers for amplification of sequences from Repro-EN-1.0.

The Repro-EN-1.0 polypeptide and immunogenic fragments of it are useful as positive controls in diagnostic assays to detect antibodies that specifically bind to Repro-EN-1.0 from patient serum samples. The polypeptides also are useful as immunogens for eliciting production of antibodies against epitopes of the protein.

The nucleotide sequence (SEQ ID NO:1) and deduced amino acid sequence (SEQ ID NO:2) of Repro-EN-1.0 follow:

```
     CGGCCGGGCTTCAGGGGCCCAGGCGCCGCTGCTGCCACCGCCATCTAACGCTGCGCCCTG
  1  ++++++++++++++++++++++++++++++++++++++++++++++++++++++++++++  60
     GCCGGCCCGAAGTCCCCGGGTCCGCGGCGACGACGGTGGCGGTAGATTGCGACGCGGGAC

GAGGCCCGGCGCGCGGATGGTGCCGGTGCGGCTCGGGTGTTGAAACGGGTGTCCCCTCCC
 61  ++++++++++++++++++++++++++++++++++++++++++++++++++++++++++++ 120
     CTCCGGGCCGCGCGCCTACCACGGCCACGCCGAGCCCACAACTTTGCCCACAGGGGAGGG

CCTCCTCCCCTCCCCCACGCGGTGGTCTCCCCTCCCACCCGGCTCAGGCAGAGCCATGTC
121  ++++++++++++++++++++++++++++++++++++++++++++++++++++++++++++ 180
     GGAGGAGGGGAGGGGGTGCGCCACCAGAGGGGAGGGTGGGCCGAGTCCGTCTCGGTACAG

M  S

TCGGGGTGGCTCCTACCCACACCTGTTGTGGGACGTGAGGAAAAGGTTCCTCGGGCTGGA
181  ++++++++++++++++++++++++++++++++++++++++++++++++++++++++++++ 240
     AGCCCCACCGAGGATGGGTGTGGACAACACCCTGCACTCCTTTTCCAAGGAGCCCGACCT

R  G  G  S  Y  P  H  L  L  W  D  V  R  K  R  F  L  G  L  E

GGACCCGTCCCGGCTGCGGAGTCGCTACCTGGGAAGAAGAGAATTTATCCAAAGATTAAA
241  ++++++++++++++++++++++++++++++++++++++++++++++++++++++++++++ 300
     CCTGGGCAGGGCCGACGCCTCAGCGATGGACCCTTCTTCTCTTAAATAGGTTTCTAATTT

D  P  S  R  L  R  S  R  Y  L  G  R  R  E  F  I  Q  R  L  K
```

```
                  -continued
     ACTTGAAGCAACCCTTAATGTGCATGATGGTTGTGTTAATACAATCTGTTGGAATGACAC
301  ++++++++++++++++++++++++++++++++++++++++++++++++++++++++++++  360
     TGAACTTCGTTGGGAATTACACGTACTACCAACACAATTATGTTAGACAACCTTACTGTG
       L  E  A  T  L  N  V  H  D  G  C  V  N  T  I  C  W  N  D  T TGGAGAATATATTTTATCTGGCTCAGATGACACCAAATTAGTAATTAGTAATCCTTACAG
361  ++++++++++++++++++++++++++++++++++++++++++++++++++++++++++++  420
     ACCTCTTATATAAAATAGACCGAGTCTACTGTGGTTTAATCATTAATCATTAGGAATGTC
       G  E  Y  I  L  S  G  S  D  D  T  K  L  V  I  S  N  P  Y  S CAGAAAGGTTTTGACAACAATTCGTTCAGGGCACCGAGCAAACATATTTAGTGCAAAGTT
421  ++++++++++++++++++++++++++++++++++++++++++++++++++++++++++++  480
     GTCTTTCCAAAACTGTTGTTAAGCAAGTCCCGTGGCTCGTTTGTATAAATCACGTTTCAA
       R  K  V  L  T  T  I  R  S  G  H  R  A  N  I  F  S  A  K  F CTTACCTTGTACAAATGATAAACAGATTGTATCCTGCTCTGGAGATGGAGTAATATTTTA
481  ++++++++++++++++++++++++++++++++++++++++++++++++++++++++++++  540
     GAATGGAACATGTTTACTATTTGTCTAACATAGGACGAGACCTCTACCTCATTATAAAAT
       L  P  C  T  N  D  K  Q  I  V  S  C  S  G  D  G  V  I  F  Y TACCAACGTTGAGCAAGATGCAGAAACCAACAGACAATGCCAATTTACGTGTCATTATGG
541  ++++++++++++++++++++++++++++++++++++++++++++++++++++++++++++  600
     ATGGTTGCAACTCGTTCTACGTCTTTGGTTGTCTGTTACGGTTAAATGCACAGTAATACC
       T  N  V  E  Q  D  A  E  T  N  R  Q  C  Q  F  T  C  H  Y  G AACTACTTATGAGATTATGACTGTACCCAATGACCCTTACACTTTTCTCTCTTGTGGTGA
600  ++++++++++++++++++++++++++++++++++++++++++++++++++++++++++++  660
     TTGATGAATACTCTAATACTGACATGGGTTACTGGGAATGTGAAAAGAGAGAACACCACT
       T  T  Y  E  I  M  T  V  P  N  D  P  Y  T  F  L  S  C  G  E AGATGGAACTGTTAGGTGGTTTGATACACGCATCAAAACTAGCTGCACAAAAGAAGATTG
661  ++++++++++++++++++++++++++++++++++++++++++++++++++++++++++++  720
     TCTACCTTGACAATCCACCAAACTATGTGCGTAGTTTTGATCGACGTGTTTTCTTCTAAC
       D  G  T  V  R  W  F  D  T  R  I  K  T  S  C  T  K  E  D  C TAAAGATGATATTTTAATTAACTGTCGACGTGCTGCCACGTCTGTTGCTATTTGCCCACC
721  ++++++++++++++++++++++++++++++++++++++++++++++++++++++++++++  780
     ATTTCTACTATAAAATTAATTGACAGCTGCACGACGGTGCAGACAACGATAAACGGGTGG
       K  D  D  I  L  I  N  C  R  R  A  A  T  S  V  A  I  C  P  P AATACCATATTACCTTGCTGTTGGTTGTTCTGACAGCTCAGTACGAATATATGATCGGCG
781  ++++++++++++++++++++++++++++++++++++++++++++++++++++++++++++  840
     TTATGGTATAATGGAACGACAACCAACAAGACTGTCGAGTCATGCTTATATACTAGCCGC
       I  P  Y  Y  L  A  V  G  C  S  D  S  S  V  R  I  Y  D  R  R AATGCTGGGCACAAGAGCTACAGGGAATTATGCAGGTCGAGGGACTACTGGAATGGTTGC
841  ++++++++++++++++++++++++++++++++++++++++++++++++++++++++++++  900
     TTACGACCCGTGTTCTCGATGTCCCTTAATACGTCCAGCTCCCTGATGACCTTACCAACG
       M  L  G  T  R  A  T  G  N  Y  A  G  R  G  T  T  G  M  V  A CCGTTTTATTCCTTCCCATCTTAATAATAAGTCCTGCAGAGTGACATCTCTGTGTTACAG
901  ++++++++++++++++++++++++++++++++++++++++++++++++++++++++++++  960
     GGCAAAATAAGGAAGGGTAGAATTATTATTCAGGACGTCTCACTGTAGAGACACAATGTC
       R  F  I  P  S  H  L  N  N  K  S  C  R  V  T  S  L  C  Y  S TGAAGATGGTCAAGAGATTCTCGTTAGTTACTCTTCAGATTACATATATCTTTTTGACCC
961  ++++++++++++++++++++++++++++++++++++++++++++++++++++++++++++  1020
     ACTTCTACCAGTTCTCTAAGAGCAATCAATGAGAAGTCTAATGTATATAGAAAAACTGGG
       E  D  G  Q  E  I  L  V  S  Y  S  S  D  Y  I  Y  L  F  D  P GAAAGATGATACAGCACGAGAACTTAAAACTCCTTCTGCGGAAGAGAGAAGAGAAGAGTT
1021 ++++++++++++++++++++++++++++++++++++++++++++++++++++++++++++  1080
     CTTTCTACTATGTCGTGCTCTTGAATTTTGAGGAAGACGCCTTCTCTCTTCTCTTCTCAA
       K  D  D  T  A  R  E  L  K  T  P  S  A  E  E  R  R  E  E  L GCGACAACCACCAGTTAAGCGTTTGAGACTTCGTGGTGATTGGTCAGATACTGGACCCAG
1081 ++++++++++++++++++++++++++++++++++++++++++++++++++++++++++++  1140
     CGCTGTTGGTGGTCAATTCGCAAACTCTGAAGCACCACTAACCAGTCTATGACCTGGGTC
       R  Q  P  P  V  K  R  L  R  L  R  G  D  W  S  D  T  G  P  R AGCAAGGCCGGAGAGTGAACGAGAACGAGATGGAGAGCAGAGTCCCAATGTGTCATTGAT
1141 ++++++++++++++++++++++++++++++++++++++++++++++++++++++++++++  1200
     TCGTTCCGGCCTCTCACTTGCTCTTGCTCTACCTCTCGTCTCAGGGTTACACAGTAACTA
       A  R  P  E  S  E  R  E  R  D  G  E  Q  S  P  N  V  S  L  M GCAGAGAATGTCTGATATGTTATCAAGATGGTTTGAAGAAGCAAGTGAGGTTGCACAAAG
1201 ++++++++++++++++++++++++++++++++++++++++++++++++++++++++++++  1260
     CGTCTCTTACAGACTATACAATAGTTCTACCAAACTTCTTCGTTCACTCCAACGTGTTTC
       Q  R  M  S  D  M  L  S  R  W  F  E  E  A  S  E  V  A  Q  S
```

-continued

```
     CAATAGAGGACGAGGAAGATCTCGACCCAGAGGTGGAACAAGTCAATCAGATATTTCAAC
1261 ++++++++++++++++++++++++++++++++++++++++++++++++++++++++++++ 1320
     GTTATCTCCTGCTCCTTCTAGAGCTGGGTCTCCACCTTGTTCAGTTAGTCTATAAAGTTG
       N  R  G  R  G  R  S  R  P  R  G  G  T  S  Q  S  D  I  S  T

TCTTCCTACGGTCCCATCAAGTCCTGATTTGGAAGTGAGTGAAACTGCAATGGAAGTAGA
1321 ++++++++++++++++++++++++++++++++++++++++++++++++++++++++++++ 1380
     AGAAGGATGCCAGGGTAGTTCAGGACTAAACCTTCACTCACTTTGACGTTACCTTCATCT
       L  P  T  V  P  S  S  P  D  L  E  V  S  E  T  A  M  E  V  D

TACTCCAGCTGAACAATTTCTTCAGCCTTCTACATCCTCTACAATGTCAGCTCAGGCTCA
1381 ++++++++++++++++++++++++++++++++++++++++++++++++++++++++++++ 1440
     ATGAGGTCGACTTGTTAAAGAAGTCGGAAGATGTAGGAGATGTTACAGTCGAGTCCGAGT
       T  P  A  E  Q  F  L  Q  P  S  T  S  S  T  M  S  A  Q  A  H

TTCGACATCATCTCCCACAGAAAGCCCTCATTCTACTCCTTTGCTATCTTCTCCAGATAG
1441 ++++++++++++++++++++++++++++++++++++++++++++++++++++++++++++ 1500
     AAGCTGTAGTAGAGGGTGTCTTTCGGGAGTAAGATGAGGAAACGATAGAAGAGGTCTATC
       S  T  S  S  P  T  E  S  P  H  S  T  P  L  L  S  S  P  D  S

TGAACAAAGGCAGTCTGTTGAGGCATCTGGACACCACACACATCATCAGTCTGATAACAA
1501 ++++++++++++++++++++++++++++++++++++++++++++++++++++++++++++ 1560
     ACTTGTTTCCGTCAGACAACTCCGTAGACCTGTGGTGTGTGTAGTAGTCAGACTATTGTT
       E  Q  R  Q  S  V  E  A  S  G  H  H  T  H  H  Q  S  D  N  N

TAATGAAAAGCTGAGCCCCAAACCAGGGACAGGTGAACCAGTTTTAAGTTTGCACTACAG
1561 ++++++++++++++++++++++++++++++++++++++++++++++++++++++++++++ 1620
     ATTACTTTTCGACTCGGGGTTTGGTCCCTGTCCACTTGGTCAAAATTCAAACGTGATGTC
       N  E  K  L  S  P  K  P  G  T  G  E  P  V  L  S  L  H  Y  S

CACAGAAGGAACAACTACAAGCACAATAAAACTGAACTTTACAGATGAATGGAGCAGTAT
1621 ++++++++++++++++++++++++++++++++++++++++++++++++++++++++++++ 1680
     GTGTCTTCCTTGTTGATGTTCGTGTTATTTTGACTTGAAATGTCTACTTACCTCGTCATA
       T  E  G  T  T  T  S  T  I  K  L  N  F  T  D  E  W  S  S  I

AGCATCAAGTTCTAGAGGAATTGGGAGCCATTGCAAATCTGAGGGTCAGGAGGAATCTTT
1681 ++++++++++++++++++++++++++++++++++++++++++++++++++++++++++++ 1740
     TCGTAGTTCAAGATCTCCTTAACCCTCGGTAACGTTTAGACTCCCAGTCCTCCTTAGAAA
       A  S  S  S  R  G  I  G  S  H  C  K  S  E  G  Q  E  E  S  F

CGTCCCACAGAGCTCAGTGCAACCACCAGAAGGAGACAGTGAAACAAAAGCTCCTGAAGA
1741 ++++++++++++++++++++++++++++++++++++++++++++++++++++++++++++ 1800
     GCAGGGTGTCTCGAGTCACGTTGGTGGTCTTCCTCTGTCACTTTGTTTTCGAGGACTTCT
       V  P  Q  S  S  V  Q  P  P  E  G  D  S  E  T  K  A  P  E  E

ATCATCAGAGGATGTGACAAAATATCAGGAAGGAGTATCTGCAGAAAACCCAGTTGAGAA
1801 ++++++++++++++++++++++++++++++++++++++++++++++++++++++++++++ 1860
     TAGTAGTCTCCTACACTGTTTTATAGTCCTTCCTCATAGACGTCTTTTGGGTCAACTCTT
       S  S  E  D  V  T  K  Y  Q  E  G  V  S  A  E  N  P  V  E  N

CCATATCAATATAACACAATCAGATAAGTTCACAGCCAAGCCATTGGATTCCAACTCAGG
1861 ++++++++++++++++++++++++++++++++++++++++++++++++++++++++++++ 1920
     GGTATAGTTATATTGTGTTAGTCTATTCAAGTGTCGGTTCGGTAACCTAAGGTTGAGTCC
       H  I  N  I  T  Q  S  D  K  F  T  A  K  P  L  D  S  N  S  G

AGAAAGAAATGACCTCAATCTTGATCGCTCTTGTGGGGTTCCAGAAGAATCTGCTTCATC
1921 ++++++++++++++++++++++++++++++++++++++++++++++++++++++++++++ 1980
     TCTTTCTTTACTGGAGTTAGAACTAGCGAGAACACCCCAAGGTCTTCTTAGACGAAGTAG
       E  R  N  D  L  N  L  D  R  S  C  G  V  P  E  E  S  A  S  S

TGAAAAAGCCAAGGAACCAGAAACTTCAGATCAGACTAGCACTGAGAGTGCTACCAATGA
1981 ++++++++++++++++++++++++++++++++++++++++++++++++++++++++++++ 2040
     ACTTTTTCGGTTCCTTGGTCTTTGAAGTCTAGTCTGATCGTGACTCTCACGATGGTTACT
       E  K  A  K  E  P  E  T  S  D  Q  T  S  T  E  S  A  T  N  E

AAATAACACCAATCCTGAGCCTCAGTTCCAAACAGAATCCACTGGGCCTTCAGCTCATGA
2041 ++++++++++++++++++++++++++++++++++++++++++++++++++++++++++++ 2100
     TTTATTGTGGTTAGGACTCGGAGTCAAGGTTTGTCTTCGGTGACCCGGAAGTCGAGTACT
       N  N  T  N  P  E  P  Q  F  Q  T  E  A  T  G  P  S  A  H  E

AGAAACATCCACCAGGGACTCTGCTCTTCAGGACACAGATGACAGTGATGATGACCCAGT
2101 ++++++++++++++++++++++++++++++++++++++++++++++++++++++++++++ 2160
     TCTTTGTAGGTGGTCCCTGAGACGAGAAGTCCTGTGTCTACTGTCACTACTACTGGGTCA
       E  T  S  T  R  D  S  A  L  Q  D  T  D  D  S  D  D  D  P  V
```

```
                 CCTGATCCCAGGTGCAAGGTATCGAGCAGGACCTGGTGATAGACGCTCTGCTGTTGCCCG
2161 ++++|++++|++++|++++|++++|++++|++++|++++|++++|++++|++++|++++| 2220
                 GGACTAGGGTCCACGTTCCATAGCTCGTCCTGGACCACTATCTGCGAGACGACAACGGGC
                   L  I  P  G  A  R  Y  R  A  G  P  G  D  R  R  S  A  V  A  R

TATTCAGGAGTTCTTCAGACGGAGAAAAGAAAGGAAAGAAATGGAAGAATTGGATACTTT
2221 ++++|++++|++++|++++|++++|++++|++++|++++|++++|++++|++++|++++| 2280
                 ATAAGTCCTCAAGAAGTCTGCCTCTTTTCTTTCCTTTCTTTACCTTCTTAACCTATGAAA
                   I  Q  E  F  F  R  R  R  K  E  R  K  E  M  E  E  L  D  T  L

GAACATTAGAAGGCCGCTAGTAAAAATGGTTTATAAAGGCCATCGCAACTCCAGGACAAT
2281 ++++|++++|++++|++++|++++|++++|++++|++++|++++|++++|++++|++++| 2340
                 CTTGTAATCTTCCGGCGATCATTTTTACCAAATATTTCCGGTAGCGTTGAGGTCCTGTTA
                   N  I  R  R  P  L  V  K  M  V  Y  K  G  H  R  N  S  R  T  M

GATAAAAGAAGCCAATTTCTGGGGTGCTAACTTTGTAATGACTGGTTCTGAGTGTGGCCA
2341 ++++|++++|++++|++++|++++|++++|++++|++++|++++|++++|++++|++++| 2400
                 CTATTTTCTTCGGTTAAAGACCCCACGATTGAAACATTACTGACCAAGACTCACACCGGT
                   I  K  E  A  N  F  W  G  A  N  F  V  M  T  G  S  E  C  G  H

CATTTTCATCTGGGATCGGCACACTGCTGAGCATTTGATGCTTCTGGAAGCTGATAATCA
2401 ++++|++++|++++|++++|++++|++++|++++|++++|++++|++++|++++|++++| 2460
                 GTAAAAGTAGACCCTAGCCGTGTGACGACTCGTAAACTACGAAGACCTTCGACTATTAGT
                   I  F  I  W  D  R  H  T  A  E  H  L  M  L  L  E  A  D  N  H

TGTGGTAAACTGCCTGCAGCCACATCCGTTTGACCCAATTTTAGCCTCATCTGGCATAGA
2461 ++++|++++|++++|++++|++++|++++|++++|++++|++++|++++|++++|++++| 2520
                 ACACCATTTGACGGACGTCGGTGTAGGCAAACTGGGTTAAAATCGGAGTAGACCGTATCT
                   V  V  N  C  L  Q  P  H  P  F  D  P  I  L  A  S  S  G  I  D

TTATGACATAAAGATCTGGTCACCATTAGAAGAGTCAAGGATTTTTAACCGAAAACTTGC
2521 ++++|++++|++++|++++|++++|++++|++++|++++|++++|++++|++++|++++| 2580
                 AATACTGTATTTCTAGACCAGTGGTAATCTTCTCAGTTCCTAAAAATTGGCTTTTGAACG
                   Y  D  I  K  I  W  S  P  L  E  E  S  R  I  F  N  R  K  L  A

TGATGAAGTTATAACTCGAAACGAACTCATGCTGGAAGAAACTAGAAACACCATTACAGT
2581 ++++|++++|++++|++++|++++|++++|++++|++++|++++|++++|++++|++++| 2640
                 ACTACTTCAATATTGAGCTTTGCTTGAGTACGACCTTCTTTGATCTTTGTGGTAATGTCA
                   D  E  V  I  T  R  N  E  L  M  L  E  E  T  R  N  T  I  T  V

TCCAGCCTCTTTCATGTTGAGGATGTTGGCTTCACTTAATCATATCCGAGCTGACCGGTT
2641 ++++|++++|++++|++++|++++|++++|++++|++++|++++|++++|++++|++++| 2700
                 AGGTCGGAGAAAGTACAACTCCTACAACCGAAGTGAATTAGTATAGGCTCGACTGGCCAA
                   P  A  S  F  M  L  R  M  L  A  S  L  N  H  I  R  A  D  R  L

GGAGGGTGACAGATCAGAAGGCTCTGGTCAAGAGAATGAAAATGAGGATGAGGAATAATA
2701 ++++|++++|++++|++++|++++|++++|++++|++++|++++|++++|++++|++++| 2760
                 CCTCCCACTGTCTAGTCTTCCGAGACCAGTTCTCTTACTTTTACTCCTACTCCTTATTAT
                   E  G  D  R  S  E  G  S  G  Q  E  N  E  N  E  D  E  E  .

AACTCTTTTTGGCAAGCACTTAAATGTTCTGAAATTTGTATAAGACATTTATTATTTTTT
2761 ++++|++++|++++|++++|++++|++++|++++|++++|++++|++++|++++|++++| 2820
                 TTGAGAAAAACCGTTCGTGAATTTACAAGACTTTAAACATATTCTGTAAATAATAAAAAA

TTTCTTTACAGAGATTTAGTGCAATTTTAAGGTTATGGTTTTTGGAGTTTTTCCCTTTTT
2821 ++++|++++|++++|++++|++++|++++|++++|++++|++++|++++|++++|++++| 2880
                 AAAGAAATGTCTCTAAATCACGTTAAAATTCCAATACCAAAAACCTCAAAAAGGGAAAAA

TTGGGATAACCTAACATTGGTTTGGAATGATTGTGTGCATGAATTTGGGAGATTGTATAA
2881 ++++|++++|++++|++++|++++|++++|++++|++++|++++|++++|++++|++++| 2940
                 AACCCTATTGGATTGTAACCAAACCTTACTAACACACGTACTTAAACCCTCTAACATATT

AACAAAACTAGCAGAATGTTTTTAAAACTTTTTGCCGTGTATGAGGAGTGCTAGAAAATG
2941 ++++|++++|++++|++++|++++|++++|++++|++++|++++|++++|++++|++++| 3000
                 TTGTTTTGATCGTCTTACAAAAATTTTGAAAAACGGCACATACTCCTCACGATCTTTTAC

CAAAGTGCAATATTTTCCCTAACCTTCAAATGTGGGAGCTTGGATCAATGTTGAAGAATA
3001 ++++|++++|++++|++++|++++|++++|++++|++++|++++|++++|++++|++++| 3060
                 GTTTCACGTTATAAAAGGGATTGGAAGTTTACACCCTCGAACCTAGTTACAACTTCTTAT

ATTTTCATCATAGTGAAAATGTTGGTTCAAATAAATTTCTACACTTGCCATTTGCATGTT
3061 ++++|++++|++++|++++|++++|++++|++++|++++|++++|++++|++++|++++| 3120
                 TAAAAGTAGTATCACTTTTACAACCAAGTTTATTTAAAGATGTGAACGGTAAACGTACAA

TGTTGCTTTCTAATTAAAGAAACTGGTTGTTTTAAGATACCCTGAAAAAAAAAAAAAAAA
3121 ++++|++++|++++|++++|++++|++++|++++|++++|++++|++++|++++|++++| 3180
                 ACAACGAAAGATTAATTTCTTTGACCAACAAAATTCTATGGGACTTTTTTTTTTTTTTTT

AAAAAAAAA
3181 ++++|++++|→ 3189
                 TTTTTTTTT
```

This 3164-base nucleotide sequence contains an open reading frame of 2580 nucleotides encoding Repro-EN-1.0 from nucleotide 176 to nucleotide 2755. The deduced amino acid sequence of Repro-EN-1.0 has 860 amino acids. Repro-EN-1.0 has a calculated molecular mass of 96.4 kD and a pI of 5.08.

The Repro-EN-1.0 gene encodes a 3.4 kb mRNA. This mRNA is expressed primarily in skeletal muscle, heart and testis, and to a lesser extent in other tissues. However, it is not detected in lung or peripheral blood mononuclear cells (PBMC). Expression of Repro-EN-1.0 is up-regulated in breast and uterine carcinomas relative to their normal counterparts. It is highly expressed in both normal fallopian tube and fallopian tube carcinoma. It is expressed in low levels in normal ovary and ovarian carcinoma. Expression of the mRNA is lower in endometrial carcinoma cell lines than in prostate adenocarcinoma cell lines.

Analysis of the deduced amino acid sequence of Repro-EN-1.0 shows no significant sequence identity with any other protein.

There is an alternately spliced variant that was isolated form a human heart cDNA library. This variant is called IB1 and is useful in the same ways as the nucleotide sequence (SEQ ID NO:1) and deduced amino acid sequence (SEQ ID NO:2) of Repro-EN-1.0. The IB1 sequence was isolated from a heart cDNA library by screening with a nucleic acid probe obtained from the Repro-EN-1.0 sequence. The IB1 sequence is different from the Repro-EN-1.0 sequence in that it contains an additional 231 by exon inserted into the cDNA sequence at position 1555. Therefore the IB1 sequence has similar properties, but is slightly larger.

The nucleotide sequence (SEQ ID NO:3) and the deduced amino acid sequence (SEQ ID NO:4) of IB1 follow:

```
        CGGCCGGGCTTCAGGGGCCCAGGCGCCGCTGCTGCCACCGCCATCTAACGCTGCGCCCTG
   1    ------------------------------------------------------------   60
        GCCGGCCCGAAGTCCCCGGGTCCGCGGCGACGACGGTGGCGGTAGATTGCGACGCGGGAC

GAGGCCCGGCGCGCGGATGGTGCCGGTGCGGCTCGGGTGTTGAAACGGGTGTCCCCTCCC
  61    ------------------------------------------------------------  120
        CTCCGGGCCGCGCGCCTACCACGGCCACGCCGAGCCCACAACTTTGCCCACAGGGGAGGG

CCTCCTCCCCTCCCCCACGCGGTGGTCTCCCCTCCCACCCGGCTCAGGCAGAGCCATGTC
 121    ------------------------------------------------------------  180
        GGAGGAGGGGAGGGGGTGCGCCACCAGAGGGGAGGGTGGGCCGAGTCCGTCTCGGTACAG
                                                               M  S

TCGGGGTGGCTCCTACCCACACCTGTTGTGGGACGTGAGGAAAAGGTTCCTCGGGCTGGA
 181    ------------------------------------------------------------  240
        AGCCCCACCGAGGATGGGTGTGGACAACACCCTGCACTCCTTTTCCAAGGAGCCCGACCT
          R  G  G  S  Y  P  H  L  L  W  D  V  R  K  R  F  L  G  L  E

GGACCCGTCCCGGCTGCGGAGTCGCTACCTGGGAAGAAGAGAATTTATCCAAAGATTAAA
 241    ------------------------------------------------------------  300
        CCTGGGCAGGGCCGACGCCTCAGCGATGGACCCTTCTTCTCTTAAATAGGTTTCTAATTT
          D  P  S  R  L  R  S  R  Y  L  G  R  R  E  F  I  Q  R  L  K

ACTTGAAGCAACCCTTAATGTGCATGATGGTTGTGTTAATACAATCTGTTGGAATGACAC
 301    ------------------------------------------------------------  360
        TGAACTTCGTTGGGAATTACACGTACTACCAACACAATTATGTTAGACAACCTTACTGTG
          L  E  A  T  L  N  V  H  D  G  C  V  N  T  I  C  W  N  D  T

TGGAGAATATATTTTATCTGGCTCAGATGACACCAAATTAGTAATTAGTAATCCTTACAG
 361    ------------------------------------------------------------  420
        ACCTCTTATATAAAATAGACCGAGTCTACTGTGGTTTAATCATTAATCATTAGGAATGTC
          G  E  Y  I  L  S  G  S  D  D  T  K  L  V  I  S  N  P  Y  S

CAGAAAGGTTTTGACAACAATTCGTTCAGGGCACCGAGCAAACATATTTAGTGCAAAGTT
 421    ------------------------------------------------------------  480
        GTCTTTCCAAAACTGTTGTTAAGCAAGTCCCGTGGCTCGTTTGTATAAATCACGTTTCAA
          R  K  V  L  T  T  I  R  S  G  H  R  A  N  I  F  S  A  K  F

CTTACCTTGTACAAATGATAAACAGATTGTATCCTGCTCTGGAGATGGAGTAATATTTTA
 481    ------------------------------------------------------------  540
        GAATGGAACATGTTTACTATTTGTCTAACATAGGACGAGACCTCTACCTCATTATAAAAT
          L  P  C  T  N  D  K  Q  I  V  S  C  S  G  D  G  V  I  F  Y

TACCAACGTTGAGCAAGATGCAGAAACCAACAGACAATGCCAATTTACGTGTCATTATGG
 541    ------------------------------------------------------------  600
        ATGGTTGCAACTCGTTCTACGTCTTTGGTTGTCTGTTACGGTTAAATGCACAGTAATACC
          T  N  V  E  Q  D  A  E  T  N  R  Q  C  Q  F  T  C  H  Y  G

AACTACTTATGAGATTATGACTGTACCCAATGACCCTTACACTTTTCTCTCTTGTGGTGA
 601    ------------------------------------------------------------  660
        TTGATGAATACTCTAATACTGACATGGGTTACTGGGAATGTGAAAAGAGAGAACACCACT
          T  T  Y  E  I  M  T  V  P  N  D  P  Y  T  F  L  S  C  G  E

AGATGGAACTGTTAGGTGGTTTGATACACGCATCAAAACTAGCTGCACAAAAGAAGATTG
 661    ------------------------------------------------------------  720
        TCTACCTTGACAATCCACCAAACTATGTGCGTAGTTTTGATCGACGTGTTTTCTTCTAAC
          D  G  T  V  R  W  F  D  T  R  I  K  T  S  C  T  K  E  D  C
```

```
           TAAAGATGATATTTTAATTAACTGTCGACGTGCTGCCACGTCTGTTGCTATTTGCCCACC
      721 ++++|++++|++++|++++|++++|++++|++++|++++|++++|++++|++++|++++| 780
           ATTTCTACTATAAAATTAATTGACAGCTGCACGACGGTGCAGACAACGATAAACGGGTGG
             K  D  D  I  L  I  N  C  R  R  A  A  T  S  V  A  I  C  P  P

AATACCATATTACCTTGCTGTTGGTTGTTCTGACAGCTCAGTACGAATATATGATCGGCG
      781 ++++|++++|++++|++++|++++|++++|++++|++++|++++|++++|++++|++++| 840
           TTATGGTATAATGGAACGACAACCAACAAGACTGTCGAGTCATGCTTATATACTAGCCGC
             I  P  Y  Y  L  A  V  G  C  S  D  S  S  V  R  I  Y  D  R  R

AATGCTGGGCACAAGAGCTACAGGGAATTATGCAGGTCGAGGGACTACTGGAATGGTTGC
      841 ++++|++++|++++|++++|++++|++++|++++|++++|++++|++++|++++|++++| 900
           TTACGACCCGTGTTCTCGATGTCCCTTAATACGTCCAGCTCCCTGATGACCTTACCAACG
             M  L  G  T  R  A  T  G  N  Y  A  G  R  G  T  T  G  M  V  A

CCGTTTTATTCCTTCCCATCTTAATAATAAGTCCTGCAGAGTGACATCTCTGTGTTACAG
      901 ++++|++++|++++|++++|++++|++++|++++|++++|++++|++++|++++|++++| 960
           GGCAAAATAAGGAAGGGTAGAATTATTATTCAGGACGTCTCACTGTAGAGACACAATGTC
             R  F  I  P  S  H  L  N  N  K  S  C  R  V  T  S  L  C  Y  S

TGAAGATGGTCAAGAGATTCTCGTTAGTTACTCTTCAGATTACATATATCTTTTTGACCC
      961 ++++|++++|++++|++++|++++|++++|++++|++++|++++|++++|++++|++++| 1020
           ACTTCTACCAGTTCTCTAAGAGCAATCAATGAGAAGTCTAATGTATATAGAAAAACTGGG
             E  D  G  Q  E  I  L  V  S  Y  S  S  D  Y  I  Y  L  F  D  P

GAAAGATGATACAGCACGAGAACTTAAAACTCCTTCTGCGGAAGAGAGAAGAGAAGAGTT
     1021 ++++|++++|++++|++++|++++|++++|++++|++++|++++|++++|++++|++++| 1080
           CTTTCTACTATGTCGTGCTCTTGAATTTTGAGGAAGACGCCTTCTCTCTTCTCTTCTCAA
             K  D  D  T  A  R  E  L  K  T  P  S  A  E  E  R  R  E  E  L

GCGACAACCACCAGTTAAGCGTTTGAGACTTCGTGGTGATTGGTCAGATACTGGACCCAG
     1081 ++++|++++|++++|++++|++++|++++|++++|++++|++++|++++|++++|++++| 1140
           CGCTGTTGGTGGTCAATTCGCAAACTCTGAAGCACCACTAACCAGTCTATGACCTGGGTC
             R  Q  P  P  V  K  R  L  R  L  R  G  D  W  S  D  T  G  P  R

AGCAAGGCCGGAGAGTGAACGAGAACGAGATGGAGAGCAGAGTCCCAATGTGTCATTGAT
     1141 ++++|++++|++++|++++|++++|++++|++++|++++|++++|++++|++++|++++| 1200
           TCGTTCCGGCCTCTCACTTGCTCTTGCTCTACCTCTCGTCTCAGGGTTACACAGTAACTA
             A  R  P  E  S  E  R  E  R  D  G  E  Q  S  P  N  V  S  L  M

GCAGAGAATGTCTGATATGTTATCAAGATGGTTTGAAGAAGCAAGTGAGGTTGCACAAAG
     1201 ++++|++++|++++|++++|++++|++++|++++|++++|++++|++++|++++|++++| 1260
           CGTCTCTTACAGACTATACAATAGTTCTACCAAACTTCTTCGTTCACTCCAACGTGTTTC
             Q  R  M  S  D  M  L  S  R  W  F  E  E  A  S  E  V  A  Q  S

CAATAGAGGACGAGGAAGATCTCGACCCAGAGGTGGAACAAGTCAATCAGATATTTCAAC
     1261 ++++|++++|++++|++++|++++|++++|++++|++++|++++|++++|++++|++++| 1320
           GTTATCTCCTGCTCCTTCTAGAGCTGGGTCTCCACCTTGTTCAGTTAGTCTATAAAGTTG
             N  R  G  R  G  R  S  R  P  R  G  G  T  S  Q  S  D  I  S  T

TCTTCCTACGGTCCCATCAAGTCCTGATTTGGAAGTGAGTGAAACTGCAATGGAAGTAGA
     1321 ++++|++++|++++|++++|++++|++++|++++|++++|++++|++++|++++|++++| 1380
           AGAAGGATGCCAGGGTAGTTCAGGACTAAACCTTCACTCACTTTGACGTTACCTTCATCT
             L  P  T  V  P  S  S  P  D  L  E  V  S  E  T  A  M  E  V  D

TACTCCAGCTGAACAATTTCTTCAGCCTTCTACATCCTCTACAATGTCAGCTCAGGCTCA
     1381 ++++|++++|++++|++++|++++|++++|++++|++++|++++|++++|++++|++++| 1440
           ATGAGGTCGACTTGTTAAAGAAGTCGGAAGATGTAGGAGATGTTACAGTCGAGTCCGAGT
             T  P  A  E  Q  F  L  Q  P  S  T  S  S  T  M  S  A  Q  A  H

TTCGACATCATCTCCCACAGAAAGCCCTCATTCTACTCCTTTGCTATCTTCTCCAGATAG
     1441 ++++|++++|++++|++++|++++|++++|++++|++++|++++|++++|++++|++++| 1500
           AAGCTGTAGTAGAGGGTGTCTTTCGGGAGTAAGATGAGGAAACGATAGAAGAGGTCTATC
             S  T  S  S  P  T  E  S  P  H  S  T  P  L  L  S  S  P  D  S

TGAACAAAGGCAGTCTGTTGAGGCATCTGGACACCACACACATCATCAGTCTGAATTTTT
     1501 ++++|++++|++++|++++|++++|++++|++++|++++|++++|++++|++++|++++| 1560
           ACTTGTTTCCGTCAGACAACTCCGTAGACCTGTGGTGTGTGTAGTAGTCAGACTTAAAAA
             E  Q  R  Q  S  V  E  A  S  G  H  H  T  H  H  Q  S  E  F  L
                                                                 ═════

AAGGGGGCCTGAGATAGCTTTGCTTCGTAAGCGCCTGCAACAACTGAGGCTTAAGAAGGC
     1561 ++++|++++|++++|++++|++++|++++|++++|++++|++++|++++|++++|++++| 1620
           TTCCCCCGGACTCTATCGAAACGAAGCATTCGCGGACGTTGTTGACTCCGAATTCTTCCG
             R  G  P  E  I  A  L  L  R  K  R  L  Q  Q  L  R  L  K  K  A
           ══════════════════════════════════════════════════════════════
           ═══════════════════════ 231 bp insert ════════════════════════
           ══════════════════════════════════════════════════════════════
```

```
                      -continued
       TGAGCAGCAGAGGCAGCAAGAGCTAGCTGCACATACCCAGCAACAGCCTTCCACTTCTGA
1621   ++++++++++++++++++++++++++++++++++++++++++++++++++++++++++++ 1680
       ACTCGTCGTCTCCGTCGTTCTCGATCGACGTGTATGGGTCGTTGTCGGAAGGTGAAGACT E  Q  Q  R  Q  Q  E  L  A  A  H  T  Q  Q  Q  P  S  T  S  D
       ═══════════════════════════════════════════════════════════════
                              231 bp insert
       ═══════════════════════════════════════════════════════════════

TCAGTCTTCTCATGAGGGCTCTTCACAGGACCCTCATGCTTCAGATTCTCCTTCTTCTGT
1681   ++++++++++++++++++++++++++++++++++++++++++++++++++++++++++++ 1740
       AGTCAGAAGAGTACTCCCGAGAAGTGTCCTGGGAGTACGAAGTCTAAGAGGAAGAAGACA

Q  S  S  H  E  G  S  S  Q  D  P  H  A  S  D  S  P  S  S  V
       ═══════════════════════════════════════════════════════════════
                              231 bp insert
       ═══════════════════════════════════════════════════════════════

GGTTAACAAACAGCTCGGATCCATGTCACTTGACGAGCAACAGGATAACAATAATGAAAA
1741   ++++++++++++++++++++++++++++++++++++++++++++++++++++++++++++ 1800
       CCAATTGTTTGTCGAGCCTAGGTACAGTGAACTGCTCGTTGTCCTATTGTTATTACTTTT

V  N  K  Q  L  G  S  M  S  L  D  E  Q  Q  D  N  N  N  E  K
       ═══════════════════════════════════════════════════════════
                      231 bp insert              ──▶

GCTGAGCCCCAAACCAGGGACAGGTGAACCAGTTTTAAGTTTGCACTACAGCACAGAAGG
1801   ++++++++++++++++++++++++++++++++++++++++++++++++++++++++++++ 1860
       CGACTCGGGGTTTGGTCCCTGTCCACTTGGTCAAAATTCAAACGTGATGTCGTGTCTTCC

L  S  P  K  P  G  T  G  E  P  V  L  S  L  H  Y  S  T  E  G

AACAACTACAAGCACAATAAAACTGAACTTTACAGATGAATGGAGCAGTATAGCATCAAG
1861   ++++++++++++++++++++++++++++++++++++++++++++++++++++++++++++ 1920
       TTGTTGATGTTCGTGTTATTTTGACTTGAAATGTCTACTTACCTCGTCATATCGTAGTTC

T  T  T  S  T  I  K  L  N  F  T  D  E  W  S  S  I  A  S  S

TTCTAGAGGAATTGGGAGCCATTGCAAATCTGAGGGTCAGGAGGAATCTTTCGTCCCACA
1921   ++++++++++++++++++++++++++++++++++++++++++++++++++++++++++++ 1980
       AAGATCTCCTTAACCCTCGGTAACGTTTAGACTCCCAGTCCTCCTTAGAAAGCAGGGTGT

S  R  G  I  G  S  H  C  K  S  E  G  Q  E  E  S  F  V  P  Q

GAGCTCAGTGCAACCACCAGAAGGAGACAGTGAAACAAAAGCTCCTGAAGAATCATCAGA
1981   ++++++++++++++++++++++++++++++++++++++++++++++++++++++++++++ 2040
       CTCGAGTCACGTTGGTGGTCTTCCTCTGTCACTTTGTTTTCGAGGACTTCTTAGTAGTCT

S  S  V  Q  P  P  E  G  D  S  E  T  K  A  P  E  E  S  S  E

GGATGTGACAAAATATCAGGAAGGAGTATCTGCAGAAAACCCAGTTGAGAACCATATCAA
2041   ++++++++++++++++++++++++++++++++++++++++++++++++++++++++++++ 2100
       CCTACACTGTTTTATAGTCCTTCCTCATAGACGTCTTTTGGGTCAACTCTTGGTATAGTT

D  V  T  K  Y  Q  E  G  V  S  A  E  N  P  V  E  N  H  I  N

TATAACACAATCAGATAAGTTCACAGCCAAGCCATTGGATTCCAACTCAGGAGAAAGAAA
2101   ++++++++++++++++++++++++++++++++++++++++++++++++++++++++++++ 2160
       ATATTGTGTTAGTCTATTCAAGTGTCGGTTCGGTAACCTAAGGTTGAGTCCTCTTTCTTT

I  T  Q  S  D  K  F  T  A  K  P  L  D  S  N  S  G  E  R  N

TGACCTCAATCTTGATCGCTCTTGTGGGGTTCCAGAAGAATCTGCTTCATCTGAAAAAGC
2161   ++++++++++++++++++++++++++++++++++++++++++++++++++++++++++++ 2220
       ACTGGAGTTAGAACTAGCGAGAACACCCCAAGGTCTTCTTAGACGAAGTAGACTTTTTCG

D  L  N  L  D  R  S  C  G  V  P  E  E  S  A  S  S  E  K  A

CAAGGAACCAGAAACTTCAGATCAGACTAGCACTGAGAGTGCTACCAATGAAAATAACAC
2221   ++++++++++++++++++++++++++++++++++++++++++++++++++++++++++++ 2280
       GTTCCTTGGTCTTTGAAGTCTAGTCTGATCGTGACTCTCACGATGGTTACTTTTATTGTG

K  E  P  E  T  S  D  Q  T  S  T  E  S  A  T  N  E  N  N  T

CAATCCTGAGCCTCAGTTCCAAACAGAAGCCACTGGGCCTTCAGCTCATGAAGAAACATC
2281   ++++++++++++++++++++++++++++++++++++++++++++++++++++++++++++ 2340
       GTTAGGACTCGGAGTCAAGGTTTGTCTTCGGTGACCCGGAAGTCGAGTACTTCTTTGTAG

N  P  E  P  Q  F  Q  T  E  A  T  G  P  S  A  H  E  E  T  S

CACCAGGGACTCTGCTCTTCAGGACACAGATGACAGTGATGATGACCCAGTCCTGATCCC
2341   ++++++++++++++++++++++++++++++++++++++++++++++++++++++++++++ 2400
       GTGGTCCCTGAGACGAGAAGTCCTGTGTCTACTGTCACTACTACTGGGTCAGGACTAGGG

T  R  D  S  A  L  Q  D  T  D  D  S  D  D  D  P  V  L  I  P

AGGTGCAAGGTATCGAGCAGGACCTGGTGATAGACGCTCTGCTGTTGCCCGTATTCAGGA
2401   ++++++++++++++++++++++++++++++++++++++++++++++++++++++++++++ 2460
       TCCACGTTCCATAGCTCGTCCTGGACCACTATCTGCGAGACGACAACGGGCATAAGTCCT

G  A  R  Y  R  A  G  P  G  D  R  R  S  A  V  A  R  I  Q  E
```

```
                F F R R R K E R K E M E E L D T L N I R
     GTTCTTCAGACGGAGAAAAGAAAGGAAAGAAATGGAAGAATTGGATACTTTGAACATTAG
2461 ++++++++++++++++++++++++++++++++++++++++++++++++++++++++++++ 2520
     CAAGAAGTCTGCCTCTTTTCTTTCCTTTCTTTACCTTCTTAACCTATGAAACTTGTAATC

R P L V K M V Y K G H R N S R T M I K E
     AAGGCCGCTAGTAAAAATGGTTTATAAAGGCCATCGCAACTCCAGGACAATGATAAAAGA
2521 ++++++++++++++++++++++++++++++++++++++++++++++++++++++++++++ 2580
     TTCCGGCGATCATTTTTACCAAATATTTCCGGTAGCGTTGAGGTCCTGTTACTATTTTCT

A N F W G A N F V M T G S E C G H I F I
     AGCCAATTTCTGGGGTGCTAACTTTGTAATGACTGGTTCTGAGTGTGGCCACATTTTCAT
2581 ++++++++++++++++++++++++++++++++++++++++++++++++++++++++++++ 2640
     TCGGTTAAAGACCCCACGATTGAAACATTACTGACCAAGACTCACACCGGTGTAAAAGTA

W D R H T A E H L M L L E A D N H V V N
     CTGGGATCGGCACACTGCTGAGCATTTGATGCTTCTGGAAGCTGATAATCATGTGGTAAA
2641 ++++++++++++++++++++++++++++++++++++++++++++++++++++++++++++ 2700
     GACCCTAGCCGTGTGACGACTCGTAAACTACGAAGACCTTCGACTATTAGTACACCATTT

C L Q P H P F D P I L A S S G I D Y D I
     CTGCCTGCAGCCACATCCGTTTGACCCAATTTTAGCCTCATCTGGCATAGATTATGACAT
2701 ++++++++++++++++++++++++++++++++++++++++++++++++++++++++++++ 2760
     GACGGACGTCGGTGTAGGCAAACTGGGTTAAAATCGGAGTAGACCGTATCTAATACTGTA

K I W S P L E E S R I F N R K L A D E V
     AAAGATCTGGTCACCATTAGAAGAGTCAAGGATTTTTAACCGAAAACTTGCTGATGAAGT
2761 ++++++++++++++++++++++++++++++++++++++++++++++++++++++++++++ 2820
     TTTCTAGACCAGTGGTAATCTTCTCAGTTCCTAAAAATTGGCTTTTGAACGACTACTTCA

I T R N E L M L E E T R N T I T V P A S
     TATAACTCGAAACGAACTCATGCTGGAAGAAACTAGAAACACCATTACAGTTCCAGCCTC
2821 ++++++++++++++++++++++++++++++++++++++++++++++++++++++++++++ 2880
     ATATTGAGCTTTGCTTGAGTACGACCTTCTTTGATCTTTGTGGTAATGTCAAGGTCGGAG

F M L R M L A S L N H I R A D R L E G D
     TTTCATGTTGAGGATGTTGGCTTCACTTAATCATATCCGAGCTGACCGGTTGGAGGGTGA
2881 ++++++++++++++++++++++++++++++++++++++++++++++++++++++++++++ 2940
     AAAGTACAACTCCTACAACCGAAGTGAATTAGTATAGGCTCGACTGGCCAACCTCCCACT

R S E G S G Q E N E N E D E E .
     CAGATCAGAAGGCTCTGGTCAAGAGAATGAAAATGAGGATGAGGAATAATAAACTCTTTT
2941 ++++++++++++++++++++++++++++++++++++++++++++++++++++++++++++ 3000
     GTCTAGTCTTCCGAGACCAGTTCTCTTACTTTTACTCCTACTCCTTATTATTTGAGAAAA

TGGCAAGCACTTAAATGTTCTGAAATTTGTATAAGACATTTATTATTTTTTTTCTTTAC
3001 ++++++++++++++++++++++++++++++++++++++++++++++++++++++++++++ 3060
     ACCGTTCGTGAATTTACAAGACTTTAAACATATTCTGTAAATAATAAAAAAAAAGAAATG

AGAGATTTAGTGCAATTTTAAGGTTATGGTTTTTGGAGTTTTTCCCTTTTTTTGGGATAA
3061 ++++++++++++++++++++++++++++++++++++++++++++++++++++++++++++ 3120
     TCTCTAAATCACGTTAAAATTCCAATACCAAAAACCTCAAAAAGGGAAAAAAACCCTATT

CCTAACATTGGTTTGGAATGATTGTGTGCATGAATTTGGGAGATTGTATAAAACAAAACT
3121 ++++++++++++++++++++++++++++++++++++++++++++++++++++++++++++ 3180
     GGATTGTAACCAAACCTTACTAACACACGTACTTAAACCCTCTAACATATTTGTTTTGA

AGCAGAATGTTTTTAAAACTTTTTGCCGTGTATGAGGAGTGCTAGAAAATGCAAAGTGCA
3181 ++++++++++++++++++++++++++++++++++++++++++++++++++++++++++++ 3240
     TCGTCTTACAAAAATTTTGAAAAACGGCACATACTCCTCACGATCTTTTACGTTTCACGT

ATATTTTCCCTAACCTTCAAATGTGGGAGCTTGGATCAATGTTGAAGAATAATTTTCATC
3241 ++++++++++++++++++++++++++++++++++++++++++++++++++++++++++++ 3300
     TATAAAAGGGATTGGAAGTTTACACCCTCGAACCTAGTTACAACTTCTTATTAAAAGTAG

ATAGTGAAAATGTTGGTTCAAATAAATTTCTACACTTGCCATTTGCATGTTGTTGCTTT
3301 ++++++++++++++++++++++++++++++++++++++++++++++++++++++++++++ 3360
     TATCACTTTTACAACCAAGTTTATTTAAAGATGTGAACGGTAAACGTACAAACAACGAAA

CTAATTAAAGAAACTGGTTGTTTTAAGATACCCTGAAAAAAAAAAAAAAAAAAAAAAAA
3361 ++++++++++++++++++++++++++++++++++++++++++++++++++++++++▶ 3420
     GATTAATTTCTTTGACCAACAAAATTCTATGGGACTTTTTTTTTTTTTTTTTTTTTTT
```

IB1 Alternately Spliced Variant from Heart Library:
  IB1 cDNA is 3,395 base pairs
  IB1 open reading frame is 2,811 nucleotides
  IB1 open reading frame maps to nucleotides 176 to 2986
  Deduced amino acid sequence of IB1 has 937 amino acids
  Calculated molecular mass of IB1 protein is 104,969 Daltons (105 kD)
  Calculated pI of IB1 protein is 5.17

Analysis of the amino acid sequence identified several amino acid motifs that will be apparent to those skilled in the art including a myb 1 DNA binding domain, a WD 40 site, an RGD cell-attachment sequence, an N-myristolylation site and several phosphorylation and glycosylation sites. Analysis also shows that the protein is largely hydrophilic. This implies that most of the amino acid sequence is exposed to the immune system and can be recognized as epitopes.

29

Analysis of expressed sequence tags (ESTs) from a public database (Genbank) identified many overlapping ESTs that, together, covered most of the Repro-EN-1.0 cDNA sequence.

III. Repro-EN-1.0 and IB1 Nucleic Acids

This invention provides recombinant polynucleotides comprising a nucleotide sequence encoding Repro-EN-1.0 and IB1 proteins, Repro-EN-1.0 and IB1 analogs or fragments of these polypeptides, as described herein. Repro-EN-1.0 or IB1 analogs include 1) immunogenic fragments of Repro-EN-1.0 or IB1; 2) homologs of Repro-EN-1.0 or IB1 from other mammals (especially primates); 3) fragments of Repro-EN-1.0 or IB1 comprising at least 5 consecutive amino acids from the sequence of Repro-EN-1.0 or IB1; 4) non-naturally occurring polypeptides whose sequences are substantially identical to Repro-EN-1.0; and 5) fusion proteins comprising a Repro-EN-1.0 or IB1 or a Repro-EN-1.0 or IB1 analog fused to a second polypeptide moiety. The polynucleotides are useful for expressing the mRNA or polypeptides they encode and in the preparation of probes or primers, among other things.

In one embodiment, the recombinant polynucleotide molecule comprises a nucleotide sequence encoding a sequence of at least 5 amino acids selected from the amino acid sequence of Repro-EN-1.0 (SEQ ID NO:2) or IB1 (SEQ ID NO:4). The nucleotide sequence can encode a sequence of at least 25 amino acids, at least 100 amino acids or at least 200 amino acids from SEQ ID NO:2 or SEQ ID NO:4. In one embodiment, the nucleotide sequence encodes an immunogenic analog. One such immunogenic analog is a polypeptide comprising an epitope that binds specifically to an antibody from serum from a subject diagnosed with endometriosis. In another embodiment, the nucleotide sequence encodes full-length native Repro-EN-1.0 or IB1 polypeptide.

The nucleotide sequence can be identical to a sequence from Repro-EN-1.0 cDNA or its complement or IB1 cDNA or its complement, or can include degenerate codons. In one embodiment of a nucleotide sequence encoding full-length Repro-EN-1.0 or IB1, the sequence is identical to the coding sequence of Repro-EN-1.0 of SEQ ID NO: 1 or IB1 of (SEQ ID NO:3). In another embodiment, the nucleotide sequence encodes a Repro-EN-1.0 or IB1 analog whose amino acid sequence is substantially identical to the amino acid sequence of Repro-EN-1.0 polypeptide (SEQ ID NO: 2) or IB1 polypeptide (SEQ ID NO:4).

In another embodiment, the polynucleotide encodes a fusion protein between Repro-EN-1.0 or IB1 polypeptide or Repro-EN-1.0 or IB1 analog amino acid sequences and a second amino acid sequence. The second amino acid sequence can be, for example, a detectable label such as a fluorescent protein, enzyme marker of protein from a two-hybrid system.

The polynucleotides of the present invention are cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA from a human endometrial carcinoma cell line using primers based on the DNA sequence of Repro-EN-1.0 of SEQ ID NO:1. One pair of primers useful for amplifying Repro-EN-1.0 DNA, including allelic variants, is:

30

```
Upstream sense:
5'-caggacacagatgacagtgat-3'    (SEQ ID NO: 5)

Downstream antisense:
5'-agagccttctgatctgtcac-3'.    (SEQ ID NO: 6)
```

A wide variety of cloning and in vitro amplification methodologies are well-known to persons of skill. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, NY, 1989). One useful format is real time PCR. See, e.g., Luch et al. (1997) *J. Molec. Endocrinol.* 18:77-85 and Arold et al., (1997) *Proc. Nat'l Acad. Sci.*, USA 94:2438-43. Polynucleotides also can be isolated by screening genomic or cDNA libraries with probes selected from the sequences of SEQ ID NO:1 under stringent hybridization conditions.

Mutant versions of the proteins can be made by site-specific mutagenesis of other polynucleotides encoding the proteins, or by random mutagenesis caused by increasing the error rate of PCR of the original polynucleotide with 0.1 mM MnCl2 and unbalanced nucleotide concentrations.

This invention also provides expression vectors, e.g., recombinant polynucleotide molecules comprising expression control sequences operatively linked to a nucleotide sequence encoding the target polypeptide. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.) Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter.

Methods for transfecting genes into mammalian cells and obtaining their expression for in vitro use or for gene therapy, are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990).

Expression vectors useful in this invention depend on their intended use. Such expression vectors must, of course, contain expression and replication signals compatible with the host cell. Expression vectors useful for expressing the protein of this invention include viral vectors such as alpha viruses, retroviruses, adenoviruses and adeno-associated viruses, plasmid vectors, cosmids, liposomes and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

In another embodiment, endogenous genes are transcribed by operatively linking them to expression control sequences supplied endogenously that recombine with genomic DNA. In one method, one provides the cell with a recombinant polynucleotide containing a targeting sequence, which permits homologous recombination into the genome upstream of the transcriptional start site of target gene; the expression control sequences; an exon of the target gene; and an unpaired splice-donor site which pairs with a splice acceptor in the target gene. Such methods are discussed in Treco et al., WO 94/12650; Treco et al., WO 95/31560 and Treco et al., WO 96/29411.

The invention also provides recombinant cells comprising an expression vector for expression of the nucleotide sequences encoding a polypeptide of this invention. Host cells can be selected for high levels of expression in order to purify the protein. Mammalian cells are preferred for this purpose, but prokaryotic cells, such as E. coli, also are useful. The cell can be, e.g., a recombinant cell in culture or a cell in vivo.

IV Polynucleotide Probes and Primers

This invention provides polynucleotide probes and primers that specifically hybridize to a sub-sequence of Repro-EN-1.0 cDNA or its complement or IB1 cDNA or its complement, under stringent hybridization conditions. The probes and primers of this invention are polynucleotides of at least 7 nucleotides, at least 10 nucleotides, at least 15 nucleotides, at least 20 nucleotides or at least 25 nucleotides. In one embodiment, the sequence of the polynucleotide is a contiguous sequence from SEQ ID NO:1 or its complement. Any suitable region of the Repro-EN-1.0 or IB1 gene may be chosen as a target for polynucleotide hybridization. Nucleotide substitutions, deletions, and additions may be incorporated into the polynucleotides as long as the characteristic ability to specifically hybridize to the target sequence or its complement is retained. Nucleotide sequence variation may result from sequence polymorphisms of various alleles, minor sequencing errors, and the like.

The probes and primers of the invention are useful as probes in hybridization assays, such as Southern and northern blots, for identifying polynucleotides having a nucleotide sequence encoding a Repro-EN-1.0 or IB1 polypeptide, and as primers for amplification procedures. The probes and primers of the invention are also useful in detecting the presence, absence or amount of Repro-EN-1.0 or IB1 in tissue biopsies and histological sections where the detection method is carried out in situ, typically after amplification of Repro-EN-1.0 or IB1 sequences using a primer set.

The probes and primers of this invention also are useful for identifying allelic forms of Repro-EN-1.0 and animal cognate genes or IB1 and animal cognate genes. Probes and primers can be used to screen human or animal genomic DNA or cDNA libraries under, e.g., stringent conditions. DNA molecules that specifically hybridize to the probe are then further examined to determine whether they are Repro-EN-1.0 allelic variants or animal cognates or IB1 allelic variants or animal cognates.

The probes also are useful in oligonucleotide arrays. Such arrays are used in hybridization assays to check the identity of bases in a target polynucleotide. In essence, when a target hybridizes perfectly to a probe on the array, the target contains the nucleotide sequence of the probe. When the target hybridizes less well, or does not hybridize at all, then the target and probe differ in sequence by one or more nucleotide. By proper selection of probes, one can check bases on a target molecule. See, e.g., Chee et al., WO 95/11995. The use the Repro-EN-1.0 or IB1 sequence in genomics is described further below.

In one embodiment, the polynucleotide is directly or indirectly detectable through a detectable moiety. A detectable moiety bound to either an oligonucleotide primer or a probe is subsequently used to detect hybridization of an oligonucleotide primer to the RNA component. Detection of labeled material bound to a Repro-EN-1.0 or IB1 polynucleotide in a sample provides a means of determining a diagnostic or prognostic value.

Although primers and probes can differ in sequence and length, the primary differentiating factor is one of function: primers serve as an initiation point for DNA synthesis of a target polynucleotide, as in RT and PCR reactions, while probes are typically used for hybridization to and detection of a target polynucleotide. Typical lengths of primers or probes can range from 7-50 nucleotides, preferably from 10-40 nucleotides, and most preferably from 15-35 nucleotides. A primer or probe can also be labeled with a detectable moiety for detection of hybridization of the primer or probe to the target polynucleotide.

In general, those of skill in the art recognize that the polynucleotides used in the invention include both DNA and RNA molecules and naturally occurring modifications thereof, as well as synthetic, non-naturally occurring analogs of the same, and heteropolymers, of deoxyribonucleotides, ribonucleotides, and/or analogs of either. The particular composition of a polynucleotide or polynucleotide analog will depend upon the purpose for which the material will be used and the environment in which the material will be placed. Modified or synthetic, non-naturally occurring nucleotides have been designed to serve a variety of purposes and to remain stable in a variety of environments, such as those in which nucleases are present.

Oligonucleotides preferably are synthesized, e.g., on an Applied BioSystems or other commercially available oligonucleotide synthesizer according to specifications provided by the manufacturer. Oligonucleotides may be prepared using any suitable method, such as the phosphotriester and phosphodiester methods, or automated embodiments thereof. In one such automated embodiment, diethylphosphoramidates are used as starting materials and may be synthesized as described by Beaucage et al., *Tetrahedron Letters* 22: 1859 (1981), and U.S. Pat. No. 4,458,066.

Polynucleotides, e.g., probes, also can be recombinantly produced through the use of plasmids or other vectors.

In one aspect this invention provides a probe that specifically hybridizes to the 5' untranslated region of Repro-EN-1.0 or IB1, the coding region of Repro-EN-1.0 or IB1, or a region of Repro-EN-1.0 or IB1 encoding an epitope of the Repro-EN-1.0 or IB1 polypeptide.

In another aspect, this invention provides a primer pair which amplifies a nucleotide sequence encoding a polypeptide epitope of Repro-EN-1.0 or IB1 recognized by an antibody from an individual diagnosed with endometriosis. A primer pair that amplifies a particular nucleotide sequence (given in the 5' to 3' orientation) includes a 5' primer and a 3' primer. The 3' primer hybridizes to the 3' end of the nucleotide sequence or downstream from it. The 5' primer hybridizes to the 3' end of the complement of the nucleotide sequence or downstream from it. In this way, the primers can amplify a polynucleotide that comprises the nucleotide sequence. One nucleotide sequence encoding a polypeptide epitope of Repro-EN-1.0 has been identified within the about 2.2 kb from 3' end of the coding sequence of Repro-EN-1.0 (SEQ ID NO: 1).

V. Methods for Detecting Repro-EN-1.0 and IB1 Polynucleotides

The probes and primers of this invention are useful, among other things, in detecting Repro-EN-1.0 or IB1 polynucleotides in a sample. A method for detecting the presence, absence or amount of a Repro-EN-1.0 or IB1 polynucleotide in a sample involves two steps: (1) specifically hybridizing a polynucleotide probe or primer to a Repro-EN-1.0 or IB1 polynucleotide, and (2) detecting the specific hybridization.

For the first step of the method, the polynucleotide used for specific hybridization is chosen to hybridize to any suitable region of Repro-EN-1.0. The polynucleotide can be a DNA or RNA molecule, as well as a synthetic, non-naturally occurring analog of the same. The polynucleotides in this step are polynucleotide primers and polynucleotide probes disclosed herein. This includes probes and primers having sequences selected from the sequence of Repro-EN-1.0 (SEQ ID NO:1) or selected from the cyber-sequence of Repro-EN-1.0 (SEQ ID NO:5).

For the second step of the reaction, any suitable method for detecting specific hybridization of a polynucleotide to Repro-EN-1.0 or IB1 may be used. Such methods include, e.g., amplification by extension of a hybridized primer using reverse transcriptase (RT); extension of a hybridized primer using RT-PCR or other methods of amplification; and in situ detection of a hybridized primer. In in situ hybridization, a sample of tissue or cells is fixed onto a glass slide and permeablized sufficiently for use with in situ hybridization techniques. Detectable moieties used in these methods include, e.g., labeled polynucleotide probes; direct incorporation of label in amplification or RT reactions, and labeled polynucleotide primers.

Often, cell extracts or tissue samples used in methods for determining the amount of a polynucleotide in a sample will contain variable amounts of cells or extraneous extracellular matrix materials. Thus, a method for determining the cell number in a sample is important for determining the relative amount per cell of a test polynucleotide such as Repro-EN-1.0 or IB1. A control for cell number and amplification efficiency is useful for determining diagnostic values for a sample of a potential cancer, and a control is particularly useful for comparing the amount of test polynucleotide such as Repro-EN-1.0 or IB1 in sample to a diagnostic value for breast cancer, uterine cancer or fallopian tube cancer. A preferred embodiment of the control RNA is endogenously expressed 28S rRNA. (See, e.g., Khan et al., Neurosci. Lett. 147: 114-117 (1992) which used 28S rRNA as a control, by diluting reverse transcribed 28S rRNA and adding it to the amplification reaction.)

VI. Inhibitory Polynucleotides for Inhibiting Repro-EN-1.0 and IB1 Expression A. General This invention also provides inhibitory polynucleotides directed against Repro-EN-1.0 or IB1 polynucleotides that inhibit Repro-EN-1.0 or IB1 expression and, therefore inhibit its activity in a cell. Inhibitory polynucleotides can inhibit Repro-EN-1.0 or IB1 activity in a number of ways. According to one mechanism, the polynucleotide prevents transcription of the Repro-EN-1.0 or IB1 gene (for instance, by triple helix formation). In another mechanism, the polynucleotide destabilizes the Repro-EN-1.0 or IB1 and reduces its half-life. In another mechanism, the polynucleotide inhibits assembly of the RNA component into the Repro-EN-1.0 or IB1 by binding to Repro-EN-1.0 or IB1.

An inhibitory polynucleotide is a polynucleotide that is capable of specifically hybridizing with a target polynucleotide and that interferes with the transcription, processing, translation or other activity the target polynucleotide. Inhibitory polynucleotides generally are single-stranded and have a sequence of at least 7, 8, 9, 10, or 11 nucleotides capable of specifically hybridizing to the target sequence. RNA sequences generally require a sequence of at least 10 nucleotides for specific hybridization. Inhibitory polynucleotides include, without limitation, antisense molecules, ribozymes, sense molecules and triplex-forming molecules. In one embodiment, the inhibitory polynucleotide is no more than about 50 nucleotides long.

While not wishing to be limited by theory, it is believed that inhibitory polynucleotides inhibit the function of a target, in part, by binding to the appropriate target sequence. An inhibitory polynucleotide can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using inhibitory polynucleotides therefore encompass a number of different approaches to altering expression of specific genes that operate by different mechanisms. These different types of inhibitory polynucleotide technology are described in C. Helene and J. Toulme, (1990) Biochim. Biophys. Acta., 1049:99-125.

Antisense polynucleotides can include deoxyribonucleotides or ribonucleotides. They can be chemically modified so as to improve stability in the body. Properties of the polynucleotide can be engineered to impart stability (e.g., nuclease resistance), tighter binding or the desired $T_m$. See, e.g., International patent publication No. 94/12633.

The general approach to constructing various polynucleotides useful in inhibitory polynucleotide therapy has been reviewed by A. R. Vander Krol et al. (1988), Biotechniques 6:958-976, and by C. A. Stein et al., (1988) Cancer Res. (1988) 48:2659-2668. See also Oligodeoxynucleotides: Antisense Inhibitors of Gene Expression, Cohen, J. S., editor, MacMillan Press, London, pages 79-196 (1989), and Antisense RNA and DNA, (1988), D. A. Melton, Ed., Cold Spring Harbor Laboratory, Cold Spring Harbor, N.Y. In certain embodiments inhibitory polynucleotides comprise a derivatized substituent which is substantially non-interfering with respect to hybridization of the inhibitory polynucleotide to the target polynucleotide.

B. Antisense

This invention provides antisense polynucleotides capable of specifically hybridizing to a target sequence of Repro-EN-1.0 or IB1. Antisense polynucleotides are useful in vitro or in vivo to inhibit the activity of Repro-EN-1.0 or IB1.

The antisense polynucleotides of this invention comprise an antisense sequence of at least 7 nucleotides that specifically hybridize to a sequence from Repro-EN-1.0 or IB1 and, more particularly, mammalian Repro-EN-1.0 or IB1 and human Repro-EN-1.0 or IB1.

The antisense sequence can be between about 10 and about 50 nucleotides or between about 15 and about 35 nucleotides. In other embodiments, antisense polynucleotides are polynucleotides of less than about 100 nucleotides or less than about 200 nucleotides. Accordingly, a sequence of the antisense polynucleotide can specifically hybridize to all or part of the Repro-EN-1.0 or IB1, such as antisense polynucleotides to the Repro-EN-1.0 or IB1 gene or its transcribed RNA. In one embodiment, the sequence of the polynucleotide contains within it the antisense sequence. In this case, the antisense sequence is contained within a polynucleotide of longer sequence. In another embodiment, the sequence of the polynucleotide consists essentially of, or is, the antisense sequence. Thus, for example, the antisense polynucleotide can be a polynucleotide of less than about 50 nucleotides in a sequence that specifically hybridizes to the target sequence.

Generally, to assure specific hybridization, the antisense sequence is substantially complementary to the target sequence in Repro-EN-1.0 or IB1. In certain embodiments, the antisense sequence is exactly complementary to the target sequence. The antisense polynucleotides may include nucleotide substitutions, additions, deletions, or transpositions, so long as specific binding to the relevant target sequence corresponding to Repro-EN-1.0 mRNA or its gene, or IB1 mRNA or its gene, is retained as a functional property of the polynucleotide.

The antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothioate, etc.), among others.

For general methods relating to antisense polynucleotides, see *Antisense RNA and DNA*, (1988), D. A. Melton, Ed., Cold Spring Harbor Laboratory, Cold Spring Harbor, N.Y.). For a review of antisense therapy, see, e.g., Uhlmann et al., *Chem. Reviews*, 90:543-584 (1990).

C. Ribozymes

Cleavage of Repro-EN-1.0 or IB1 can be induced by the use of ribozymes or catalytic RNA. In this approach, the ribozyme would contain either naturally occurring RNA (ribozymes) or synthetic nucleic acids with catalytic activity. Bratty et al., (1992) *Biochim. Biophys. Acta.*, 1216:345-59 (1993) and Denhardt, (1992) *Ann. N.Y. Acad. Sci.*, 660:70-76 describe methods for making ribozymes.

Unlike the antisense and other polynucleotides described above, which bind to an RNA or a DNA, a ribozyme not only binds but also specifically cleaves and thereby potentially inactivates a target RNA. Such a ribozyme can comprise 5'- and 3'-terminal sequences complementary to the Repro-EN-1.0 RNA or IB1 RNA.

Optimum target sites for ribozyme-mediated inhibition of activity can be determined as described by Sullivan et al., PCT patent publication No. 94/02595 and Draper et al., PCT patent publication No. 93/23569. As described by Hu et al., PCT patent publication No. 94/03596, antisense and ribozyme functions can be combined in a single polynucleotide. Upon review of the RNA sequence of Repro-EN-1.0 and IB1, those in the art will note that several useful ribozyme target sites are present and susceptible to cleavage by, for example, a hammerhead motif ribozyme.

Such engineered ribozymes can be expressed in cells or can be transferred by a variety of means (e.g., liposomes, immunoliposomes, biolistics, direct uptake into cells, etc.). Other forms of ribozymes (group I intron ribozymes (Cech (1995) *Biotechnology*, 13; 323); hammerhead ribozymes (Edgington (1992) *Biotechnology* 10: 256) can be engineered on the basis of the disclosed Repro-EN-1.0 or IB1 sequence information to catalyze cleavage of Repro-EN-1.0 RNA or IB1 RNA. Moreover, ribozymes can comprise one or more modified nucleotides or modified linkages between nucleotides, as described above.

D. Other Inhibitory Polynucleotides

In addition to the antisense and ribozyme inhibitory polynucleotides, one can construct polynucleotides that will bind to duplex nucleic acid either in the folded RNA component or in the gene for the RNA component, forming a triple helix-containing or triplex nucleic acid to inhibit Repro-EN-1.0 or IB1 activity. Such polynucleotides of the invention are constructed using the base-pairing rules of triple helix formation and the nucleotide sequence of the RNA component (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci.* (U.S.A.) 83: 9591. Such polynucleotides can block Repro-EN-1.0 or IB1 activity in a number of ways, including by preventing transcription of the Repro-EN-1.0 or IB1 gene.

Typically, and depending on mode of action, the triplex-forming polynucleotides of the invention comprise a sequence large enough to form a stable triple helix but small enough, depending on the mode of delivery, to administer in vivo.

E. Methods for Making Inhibitory Polynucleotides

Inhibitory polynucleotides can be made chemically or recombinantly.

1. Chemical Synthesis

Small inhibitory polynucleotides for direct delivery can be made by chemical synthesis. Chemically synthesized polynucleotides can be DNA or RNA, or can include nucleotide analogs or backbones that are not limited to phosphodiester linkages.

2. Recombinant Production

For delivery into cells or for gene therapy methods, recombinant production of inhibitory polynucleotides through the use of expression vectors is particularly useful. Accordingly, this invention also provides expression vectors, e.g., recombinant polynucleotide molecules comprising expression control sequences operatively linked to the nucleotide sequence encoding the inhibitory polynucleotide.

VII. Repro-EN-1.0 and IB1 Polypeptides

This invention also provides purified, recombinant Repro-EN-1.0 and IB1 polypeptide, and Repro-EN-1.0 and IB1 analogs. Recombinant Repro-EN-1.0 polypeptide includes the polypeptide whose amino acid sequence is presented in SEQ ID NO:2, as well as allelic variants of it. Repro-EN-1.0 analogs include 1) immunogenic fragments of Repro-EN-1.0; 2) homologs of Repro-EN-1.0 from other mammals (especially primates); 3) fragments of Repro-EN-1.0 comprising at least 5 consecutive amino acids from the sequence of Repro-EN-1.0; 4) non-naturally occurring polypeptides whose sequences are substantially identical to Repro-EN-1.0; and 5) fusion proteins comprising a Repro-EN-1.0 or a Repro-EN-1.0 analog fused to a second polypeptide moiety.

Repro-EN-1.0 polypeptide refers to native Repro-EN-1.0, the polypeptide whose amino acid sequence is the amino acid sequence of SEQ ID NO:2, and to allelic variants of it. Polynucleotide molecules that encode allelic variants of Repro- EN-1.0 are isolatable from endometrial cancer cell cDNA or genomic DNA and typically hybridize under stringent conditions to the nucleotide sequence encoding Repro-EN-1.0 (SEQ ID NO: 1). They can be obtained by amplification using, e.g., PCR primers taken from the sequence of Repro-EN-1.0 described herein.

Repro-EN-1.0 polypeptides are useful as immunogens to elicit the production of anti-Repro-EN-1.0 antibodies, as affinity capture molecules to isolate such antibodies from a mixture, and as controls in diagnostic methods aimed at detecting Repro-EN-1.0 in a sample.

Immunogenic Repro-EN-1.0 analogs are polypeptides having a sequence of at least 5 amino acids selected from native Repro-EN-1.0 and which, when presented to an animal as an immunogen, elicit a humoral or cell-mediated immune response. This includes polypeptides comprising an amino acid sequence which is an epitope from Repro-EN-1.0, such as immunogenic fragments of Repro-EN-1.0. Repro-EN-1.0 protein analogs optionally are in isolated form. Persons skilled in the art are familiar with methods of identifying probable epitopes of a protein. For example, polypeptide fragments most likely to elicit an immune response against the native protein are those that exist on the surface of the native protein. Portions of a protein on the surface tend to include hydrophilic amino acids. Such regions can be identified by inspection or with available software. In one embodiment immunogenic polypeptide is a polypeptide comprising a sequence of at least 5 consecutive hydrophilic amino acids, or at least five hydrophilic amino acids in a series of eight consecutive amino acids. Repro-EN-1.0 contains long hydrophilic stretches. Examples of such polypeptides include those comprising the sequences:

```
    KTPSAEERR,      (SEQ ID NO: 7)

RARPESER,       (SEQ ID NO: 8)

RMSDMLSR        (SEQ ID NO: 9)
    or

NEKLSPKPG.      (SEQ ID NO: 10)
```

The cDNA encoding Repro-EN-1.0 of SEQ ID NO: 1 was discovered by screening an expression library of cDNA from an endometrial carcinoma cell line with serum pooled from subjects diagnosed with endometriosis. Therefore, polypeptides comprising an epitope of Repro-EN-1.0 can be identified by screening with such serum. Preferably, the test serum is a serum pooled from several subjects positively diagnosed with endometriosis. At least one epitope of Repro-EN-1.0 exists in a fragment of 567 amino acids from the carboxy-terminus of the molecule (amino acids 293-860 of SEQ ID NO:2). At least one epitope of IB1 exists in a fragment of 644 amino acids from the carboxy terminus of the molecule (amino acids 293-937 of SEQ ID NO:4). Immunogenic fragments are useful, for example, to detect the presence of antibodies against Repro-EN-1.0 or IB1 in patient serum samples. This test is useful in diagnosis because the presence of such antibodies is a diagnostic marker for endometriosis.

Fragments of Repro-EN-1.0 or IB1 include those having at least 5 amino acids, at least 10 amino acids, at least 50 amino acids, at least 100 amino acids or at least 200 amino acids in a sequence from Repro-EN-1.0 or IB1. Fragments are useful as immunogens to produce an iminune response against Repro-EN-1.0 or IB1 in the production of antibodies. Alternatively, fragments having appropriate amino acid motifs are useful as agretopes to bind with MHC molecules. Such complexes are useful in inducing anergy against Repro-EN-1.0 or IB1.

Non-naturally occurring analogs of Repro-EN-1.0 or IB1 have at least 90% sequence identity with Repro-EN-1.0 or IB1. They can be made by, for example, introducing conservative amino acid substitutions into the sequence of Repro-EN-1.0 or IB1. Such molecules are useful as decoys or as active analogs.

Homologs of Repro-EN-1.0 or IB1 from other animals generally have sequences that are substantially identical to that of SEQ ID NO:1 or SEQ ID NO:3. Genomic DNA or cDNA encoding them can be identified through screening libraries under stringent hybridization conditions using a Repro-EN-1.0 or IB1 probe of this invention.

Fusion proteins include a fragment of Repro-EN-1.0 or IB1 fused to a second polypeptide moiety at the carboxy or amino terminus. The second polypeptide can function, for example, as a detectable label. Such markers include fluorescent protein, enzyme marker of protein from a two-hybrid system.

Repro-EN-1-0 or IB1 and analogs are most easily produced recombinantly, as described herein. Recombinant Repro-EN-1.0 or IB1 can be purified by affinity purification. In one method, recombinant Repro-EN-1.0 or IB1 analogs comprise a polyhistidine tag. The protein is purified on a nickel-chelate affinity matrix. In another method, Repro-EN-1.0 or IB1 is purified using an affinity matrix carrying anti-Repro-EN-1.0 or IB1 antibodies.

VIII. Antibodies and Hybridomas

In one aspect this invention provides a composition comprising an antibody that specifically binds Repro-EN-1.0 or IB1 polypeptides. Antibodies preferably have affinity of at least $10^6$ $M^{-1}$, $10^7$ $M^{-1}$, $10^8$ $M^{-1}$, or $10^9$ $M^{-1}$. This invention contemplates both polyclonal and monoclonal antibody compositions.

In one embodiment this invention provides immunotoxins against Repro-EN-1.0- or IB1-expressing cells. Immunotoxins are antibodies and the like as described herein coupled to a compound, e.g., a toxin, that is toxic to a target cell. Toxins can include, for example, radioactive isotopes, ricin, cisplatin, antisense molecules, *Diphtheria* toxin, *Pseudomonas* exotoxin A or *Bacillus anthraces* protective antigen. Immunotoxins bind to cancer cells that express Repro-EN-1.0 or IB1 and kill them. They are useful in the therapeutic methods of this invention. The antibodies of the invention have many uses. For example, such antibodies are useful for detecting Repro-EN-1.0 or IB1 polypeptides in immunoassays. The antibodies also can be used to screen expression libraries for particular expression products such as mammalian Repro-EN-1.0 or IB1. These are useful for detecting or diagnosing various pathological conditions related to the presence of the respective antigens. Usually the antibodies in such a procedure are labeled with a moiety allowing easy detection of presence of antigen by antibody binding. Antibodies raised against Repro-EN-1.0 or IB1 can also be used to raise anti-idiotypic antibodies.

A. Production of Antibodies

A number of immunogens are used to produce antibodies that specifically bind Repro-EN-1.0 or IB1 polypeptides. Full-length Repro-EN-1.0 or IB1 is a suitable immunogen. Typically, the immunogen of interest is a peptide of at least about 3 amino acids, more typically the peptide is 5 amino acids in length, preferably, the fragment is 10 amino acids in length and more preferably the fragment is 15 amino acids in length or greater. The peptides can be coupled to a carrier protein (e.g., as a fusion protein), or are recombinantly expressed in an immunization vector. Antigenic determinants on peptides to which antibodies bind are typically 3 to 10 amino acids in length. Naturally occurring polypeptides are also used either in pure or impure form.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods for producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immuriogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, N.Y.; and Harlow and Lane (1989) *Antibodies: A Laboratory Manual* Cold Spring Harbor Press, NY.

Antibodies, including binding fragments and single chain recombinant versions thereof, against predetermined fragments of Repro-EN-1.0 or IB1 proteins are raised by immunizing animals, e.g., with conjugates of the fragments with carrier proteins as described above.

Monoclonal antibodies are prepared from cells secreting the desired antibody. These antibodies are screened for binding to normal or modified polypeptides, or screened for agonistic or antagonistic activity, e.g., activity mediated through Repro-EN-1.0 or IB1. In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495-497.

Other suitable techniques involve selection of libraries of recombinant antibodies in phage or similar vectors. See, Huse et al. (1989) *Science* 246: 1275-1281; and Ward, et al. (1989) *Nature* 341: 544-546.

Also, recombinant immunoglobulins may be produced. See, Cabilly, U.S. Pat. No. 4,816,567; and Queen et al. (1989) *Proc. Nat'l Acad. Sci*. USA 86: 10029-10033.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Thus, an antibody used for detecting an analyte can be directly labeled with a detectable moiety, or may be indirectly labeled by, for example, binding to the antibody a secondary antibody that is, itself directly or indirectly labeled.

The antibodies of this invention are also used for affinity chromatography in isolating Repro-EN-1.0 or IB1 proteins. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified Repro-EN-1.0 or IB1 polypeptides are released.

An alternative approach is the generation of humanized immunoglobulins by linking the CDR regions of non-human antibodies to human constant regions by recombinant DNA techniques. See Queen et al., U.S. Pat. No. 5,585,089.

A further approach for isolating DNA sequences which encode a human monoclonal antibody or a binding fragment thereof is by screening a DNA library from human B cells according to the general protocol outlined by Huse et al., *Science* 246:1275-1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phage display technology can also be used to mutagenize CDR regions of antibodies previously shown to have affinity for Repro-EN-1.0 or IB1 protein receptors or their ligands. Antibodies having improved binding affinity are selected.

In another embodiment of the invention, fragments of antibodies against Repro-EN-1.0 or IB1 protein or protein analogs are provided. Typically, these fragments exhibit specific binding to the Repro-EN-1.0 protein receptor similar to that of a complete immunoglobulin. Antibody fragments include separate heavy chains, light chains Fab, Fab' $F(ab')_2$ and Fv. Fragments are produced by recombinant DNA techniques, or by enzymic or chemical separation of intact immunoglobulins.

IX. Methods for Detecting Repro-EN-1.0 and IB1 Polypeptides

Repro-EN-1.0 or IB1 polypeptides can be identified by any methods known in the art. In one embodiment, the methods involve detecting the polypeptide with a ligand that specifically recognizes the polypeptide (e.g., an immunoassay). The antibodies of the invention are particularly useful for specific detection of Repro-EN-1.0 or IB1 polypeptides. A variety of antibody-based detection methods are known in the art. These include, for example, radioimmunoassay, sandwich immunoassays (including ELISA), immunofluorescent assays, western blot, affinity chromatography (affinity ligand bound to a solid phase), and in situ detection with labeled antibodies. Another method for detecting Repro-EN-1.0 or IB1 polypeptides involves identifying the polypeptide according to its mass through, for example, gel electrophoresis, mass spectrometry or HPLC. Subject samples can be taken from any number of appropriate sources, such as saliva, peritoneal fluid, blood or a blood product (e.g., serum), urine, tissue biopsy (e.g., lymph node tissue), etc.

a. Immunoassays

The present invention also provides methods for detection of Repro-EN-1.0 or IB1 polypeptides employing one or more anti-Repro-EN-1.0 or IB1 antibody reagents (i.e., immunoassays). A number of well established immunological binding assay formats suitable for the practice of the invention are known (see, e.g., U.S. Pat. Nos. 4,366,241; 4,376,110; 4,517,288; and 4,837,168). See, e.g., METHODS IN CELL BIOLOGY VOLUME 37: ANTIBODIES IN CELL BIOLOGY, Asai, ed. Academic Press, Inc. New York (1993); BASIC AND CLINICAL IMMUNOLOGY 7th Edition, Stites & Ten, eds. (1991); Harlow and Lane, supra [e.g., Chapter 14], and Ausubel et al., supra, [e.g., Chapter 11]. Typically, immunological binding assays (or immunoassays) utilize a "capture agent" to specifically bind to and, often, immobilize the analyte to a solid phase. In one embodiment, the capture agent is a moiety that specifically binds to a Repro-EN-1.0 or IB1 polypeptide or subsequence, such as an anti-Repro-EN-1.0 or anti-IB1 antibody.

Usually the Repro-EN-1.0 or IB1 polypeptide being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-Repro-EN-1.0 or anti-IB1 antibody), or may be attached to a third moiety, such as another antibody, that specifically binds to the Repro-EN-1.0 polypeptide.

The present invention provides methods and reagents for competitive and noncompetitive immunoassays for detecting Repro-EN-1.0 or IB1 polypeptides. Non-competitive immunoassays are assays in which the amount of captured analyte (in this case Repro-EN-1.0 or IB1) is directly measured. One such assay is a two-site, monoclonal-based immunoassay utilizing monoclonal antibodies reactive to two non-interfering epitopes on the Repro-EN-1.0 or IB1 protein. See, e.g., Maddox et al., 1983, J. Exp. Med., 158:1211 for background information. In one preferred "sandwich" assay, the capture agent (e.g., an anti-Repro-EN-1.0 or anti-IB1 antibody) is bound directly to a solid substrate where it is immobilized. These immobilized antibodies then capture any Repro-EN-1.0 or IB1 protein present in the test sample. The Repro-EN-1.0 or IB1 polypeptide thus immobilized can then be labeled, i.e., by binding to a second anti-Repro-EN-1.0 or IB1 antibody bearing a label. Alternatively, the second anti-Repro-EN-1.0 or IB1 antibody may lack a label, but be bound by a labeled third antibody specific to antibodies of the species from which the second antibody is derived. The second antibody alternatively can be modified with a detectable moiety, such as biotin, to which a third labeled molecule can specifically bind, such as enzyme-labeled streptavidin.

In competitive assays, the amount of Repro-EN-1.0 or IB1 protein present in the sample is measured indirectly by measuring the amount of an added (exogenous) Repro-EN-1.0 or IB1 displaced (or competed away) from a capture agent (e.g., anti-Repro-EN-1.0 or anti-IB1 antibody) by the Repro-EN-1.0 or IB1 protein present in the sample.

A hapten inhibition assay is another example of a competitive assay. In this assay Repro-EN-1.0 or IB1 protein is immobilized on a solid substrate. A known amount of anti-Repro-EN-1.0 or anti-IB1 antibody is added to the sample, and the sample is then contacted with the immobilized Repro-EN-1.0 or IB1 protein. In this case, the amount of anti-Repro-EN-1.0 or anti-IB1 antibody bound to the immobilized Repro-EN-1.0 or IB1 protein is inversely proportional to the amount of Repro-EN-1.0 protein present in the sample. The amount of immobilized antibody may be detected by detecting either the immobilized fraction of antibody or the fraction of the antibody that remains in solution. In this aspect, detection may be direct, where the antibody is labeled, or indirect where the label is bound to a molecule that specifically binds to the antibody as described above.

b. Other Antibody-Based Assay Formats

The invention also provides reagents and methods for detecting and quantifying the presence of Repro-EN-1.0 or IB1 polypeptide in the sample by using an immunoblot (Western blot) format. Another immunoassay is the so-called "lateral flow chromatography." In a non-competitive version of lateral flow chromatography, a sample moves across a substrate by, e.g., capillary action, and encounters a mobile labeled antibody that binds the analyte forming a conjugate. The conjugate then moves across the substrate and encounters an immobilized second antibody that binds the analyte. Thus, immobilized analyte is detected by detecting the labeled antibody. In a competitive version of lateral flow chromatography a labeled version of the analyte moves across the carrier and competes with unlabeled analyte for binding with the immobilized antibody. The greater the amount of the analyte in the sample, the less the binding by labeled analyte and, therefore, the weaker the signal. See, e.g., May et al., U.S. Pat. No. 5,622,871 and Rosenstein, U.S. Pat. No. 5,591,645.

c. Solid Phases: Substrates, Solid Supports, Membranes, Filters

As noted supra, depending upon the assay, various components, including the antigen, target antibody, or anti-Repro-EN-1.0 or anti-IB1 antibody, may be bound to a solid surface or support (i.e., a substrate, membrane, or filter paper). Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

d. Mass Spectrometry

The mass of a molecule frequently can be used as an identifier of the molecule. Therefore, methods of mass spectrometry can be used to identify a protein analyte. Mass spectrometers can measure mass by determining the time required for an ionized analyte to travel down a flight tube and to be detected by an ion detector.

One method of mass spectrometry for proteins is matrix-assisted laser desorption/ionization mass spectrometry ("MALDI"). In MALDI the analyte is mixed with an energy absorbing matrix material that absorbs energy of the wavelength of a laser and placed on the surface of a probe. Upon striking the matrix with the laser, the analyte is desorbed from the probe surface, ionized, and detected by the ion detector. See, for example, Hillenkamp et al., U.S. Pat. No. 5,118,937.

Other methods of mass spectrometry for proteins are described in Hutchens and Yip, U.S. Pat. No. 5,719,060. In one such method referred to as Surfaces Enhanced for Affinity Capture ("SEAC") a solid phase affinity reagent that binds the analyte specifically or non-specifically, such as an antibody or a metal ion, is used to separate the analyte from other materials in a sample. Then the captured analyte is desorbed from the solid phase by, e.g., laser energy, ionized, and detected by the detector.

e. Assay Combinations

The diagnostic and prognostic assays described herein can be carried out in various combinations and can also be carried out in conjunction with other diagnostic or prognostic tests. For example, when the present methods are used to diagnose endometriosis, the presence of a Repro-EN-1.0 or IB1 polypeptide can be used to determine the stage of the disease. Tests that may provide additional information include microscopic analysis of biopsy samples, detection of antigens (e.g., cell-surface markers) associated with endometriosis (e.g., using histocytochemistry, FACS, or the like).

X. Diagnostic, Monitoring and Prognostic Methods

A. Methods of Diagnosing Endometriosis

We have detected circulating antibodies against Repro-EN-1.0 or IB1 in the blood of women diagnosed with endometriosis. This supports the idea that endometriosis has an autoimmune component. Further, Repro-EN-1.0 or IB1 and auto-antibodies against Repro-EN-1.0 or IB1 represent two targets in the diagnosis of endometriosis.

Repro-EN-1.0 or IB1 that is shed into the peritoneal fluid of women with endometriosis is useful in methods of diagnosing endometriosis. These methods include detecting Repro-EN-1.0 or IB31 in a biological sample of a subject. Suitable samples include, without limitation, saliva, blood or a blood product (e.g., serum), urine, menstrual fluid, vaginal secretion and, in particular, peritoneal fluid. Repro-EN-1.0 or IB1 can be detected by any of the methods described herein. Any detection of Repro-EN-1.0 or IB1 above a normal range is a positive sign in the diagnosis of endometriosis.

In another aspect, this invention provides methods for diagnosing endometriosis in a subject by detecting in a sample from the subject a diagnostic amount of an antibody that specifically binds to Repro-EN-1.0 or IB1 polypeptide. Suitable patient samples include, without limitation, saliva, blood or a blood product (e.g., serum), peritoneal fluid, urine, menstrual fluid, vaginal secretion. The antibodies can be detected by any of the methods for detecting proteins described herein. However, sandwich type assays are particularly useful. In one version, all antibodies are captured onto a solid phase, for example using protein A, and antibodies specific for Repro-EN-1.0 or IB1 are detected using a directly or indirectly labeled Repro-EN-1.0 or IB1 or polypeptide fragment of it having an epitope of Repro-EN-1.0 or IB1. In another version of the assay, Repro-EN-1.0 or IB1 or an antigenic fragment of it can be used as the capture molecule and captured antibodies can be detected.

While the detection of antibodies, in general, against Repro-EN-1.0 or IB1 is a positive sign of endometriosis, IgE an $IgG_4$ class antibodies are particularly specific and sensitive for the diagnosis of endometriosis. Therefore, in one embodiment, the diagnostic method involves specifically detecting IgE or $IgG_4$ antibodies that specifically recognize Repro-EN-1.0 or IB1. Anti-human IgE antibodies and anti-human $IgG_4$ antibodies can be easily bought or made.

1. In Vivo Diagnosis

In another method of the invention, endometriosis can be diagnosed in vivo. The methods involve detecting Repro-EN-1.0 or IB1 in the body, e.g., in the peritoneum. In general, any conventional method for visualizing diagnostic imaging can be used.

In one method for diagnosing endometriosis, detection is performed by laparoscopy. A ligand specific for Repro-EN-1.0 or IB1 is introduced into the subject at the site of a suspected lesion and binding is detected using the laparoscope. Alternatively, the binding can be detected by, for example, magnetic resonance imaging (MRI) or electron spin resonance (ESR). Usually gamma-emitting and positron-emitting radioisotopes are used for camera imaging and paramagnetic isotopes are used for magnetic resonance imaging. Any amount of binding above background is a positive sign of endometriosis. Persons of skill in the art recognize that not every positive sign results in a definitive diagnosis of a disease.

Endometriotic lesions can be removed surgically. However, lesions may be tiny, and difficult to identify by eye. This invention takes advantage of Repro-EN-1.0 or IB1 as marker for endometriosis by providing a method to identify and remove endometriotic lesions. The method involves identifying endometriotic lesions in situ using a labeled probe directed to Repro-EN-1.0 or IB1. Then, the lesions are removed surgically.

In the practice of this method, a probe is provided. The probe binds to Repro-EN-1.0 or IB1 and is labeled with a detectable marker that can be detected in a surgical procedure. In particular, the probe can be an antibody that specifically binds Repro-EN-1.0 or IB1. Preferred labels that can be detected during surgery are radioactive labels and fluorescent labels. Radioactive labels can be detected with the use of, e.g., a Geiger counter. Fluorescent labels, such as FITC, can be detected using, e.g., a D-Light-System (Storz, Tuttlingen Germany).

Surgery can proceed as follows. The labeled probe is introduced into the peritoneum of the patient for a time sufficient for the label to bind to endometriotic lesions. Unbound labeled probe is washed out. Then, endometriotic lesions are identified using a suitable detector. For example, in laparoscopic surgery, a Geiger counter may be introduced through the incision. Radioactive ("hot") spots indicate bound labeled and, therefore, an endometriotic lesion. These lesions are then removed from the patient.

B. Methods of Diagnosing Cancer

Repro-EN-1.0 or IB1 is up-regulated in breast cancer cells, uterine cancer cells, and prostate cancer cells. Therefore, Repro-EN-1.0 or IB1 is a marker for these pathologic conditions. Accordingly, the methods described herein for detecting Repro-EN-1.0 or IB1 polynucleotides or Repro-EN-1.0 or IB1 polypeptides in a sample are useful in methods for diagnosing these cancers, monitoring their progress or treatment, and determining patient prognosis. The methods of the present invention allow cancerous conditions to be detected with increased confidence and at an earlier stage, before cells are detected as cancerous based on pathological characteristics. It is, of course, understood by diagnosticians that diagnostic tests are measured by their degree of specificity and sensitivity. Tests which are not perfectly specific or sensitive are, nevertheless, useful in diagnosis because they provide useful information which, in combination with other evidence, can provide a definitive diagnosis or indicate a course of treatment.

Methods for diagnosis involve determining a diagnostic amount of Repro-EN-1.0 or IB1 (e.g., mRNA, cDNA or polypeptide) in a patient sample and comparing that amount with a normal range (e.g., a control amount) expected to be found in the sample. The samples used to determine the normal range of Repro-EN-1.0 or IB1 can be normal samples from the individual to be tested, or normal samples from other individuals not suffering from the disease condition.

A variety of patient samples can be used in the methods of the invention. For example, cell extracts, cultured cells, or tissue samples provide convenient samples for use with the methods of the invention. The methods of the invention can use samples either in solution or extracts, for example, with RT-PCR, or samples such as tissue sections for in situ methods of detection. Samples can also be obtained from sources such as fine-needle biopsies, e.g., from breast, uterus or prostate; cellular materials; whole cells; tissue and cell extracts; RNA extracted from tissue and cells and histological sections of tissue.

Methods for monitoring the course of a cancer with which Repro-EN-1.0 or IB1 is associated involve determining the amount of Repro-EN-1.0 or IB1 in a sample at a first and second time. The times can be during routine physical examinations or during a course of treatment for the cancer. As cancer appears and/or progresses, the amount of Repro-EN-1.0 or IB1 in a sample is expected to increase. Regression or cure of the cancer are accompanied by a decrease or elimination of Repro-EN-1.0 or IB1 in a sample.

The diagnostic and prognostic methods can also be carried out in conjunction with other diagnostic or prognostic tests. In some instances, such combination tests can provide useful information regarding the progression of a disease, although the present methods for testing for Repro-EN-1.0 or IB1 provide much useful information in this regard.

Another diagnostic method of the invention involves the administration to a subject of a labeled composition that specifically binds to cells bearing Repro-EN-1.0, or IB1 such as labelled antibodies. Then, the localization of the label is determined by any of the known radiologic methods. Any conventional method for visualizing diagnostic imaging can be used. Usually gamma- and positron-emitting radioisotopes are used for camera imaging and paramagnetic isotopes are used for MRI.

C. Methods of Diagnosing Chromosomal Changes

The Repro-EN-1.0 or IB1 gene is located on chromosome 1. A translocation at this site can result in alteration of Repro-EN-1.0 or IB1 activity, such as activated transcription or changed function. Chromosomal translocations in the vicinity of the Repro-EN-1.0 or IB1 gene can be detected by hybridizing a labeled probe of this invention to a chromosome spread. A translocation, duplication or deletion can be identified by aberrant hybridization patterns compared to normal. Such tests are useful in detecting genetic abnormalities such as familial disposition to breast, uterine or prostate cancer, or early onset of the disease. A method for fluorescent in situ hybridization of chromosomes is provided in the Examples.

The present invention also provides for kits for performing the diagnostic and prognostic method of the invention. Such kits include a polynucleotide probe or primer, or an antibody specific for Repro-EN-1.0 or IB1 and instructions to use the reagents to detect Repro-EN-1.0 or IB1 in a patient sample.

XI. Methods for Inhibiting Repro-EN-1.0 or IB1 Expression or Activity and of Treating Cancer Inhibiting Repro-EN-1.0 or IB1 expression or activity in a breast, uterine or prostate cancer cell can alter the rate of growth or aggressiveness of the cancer. Inhibiting Repro-EN-1.0 or IB1 expression or activity is useful in vivo in the prophylactic and therapeutic treatment of prostate cancer or other conditions involving Repro-EN-1.0 or IB1 expression. Accordingly, this invention provides methods for inhibiting Repro-EN-1.0 or IB1 expression or activity. The methods involve contacting a prostate cancer cell, in vitro or in vivo, with an inhibitory polynucleotide, an immunotoxin or another compound that inhibits Repro-EN-1.0 or IB1 expression or activity.

A. Delivery of Inhibitory Polynucleotides

This invention contemplates a variety of means for delivering an inhibitory polynucleotide to a subject including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. Methods useful for delivery of polynucleotides for therapeutic for therapeutic purposes are described in Inouye et al., U.S. Pat. No. 5,272,065.

B. Pharmaceutical Compositions and Treatment

Agents, such as inhibitory polynucleotides, immunotoxins or other compounds that inhibit Repro-EN-1.0 or IB1 expression or activity preferably are delivered in pharmaceutical compositions comprising the agent and a pharmaceutically acceptable carrier. The agent can be administered by any route that gives it access to cells expressing Repro-EN-1.0 or IB1, for example, prostate tumor cells. This includes, for example, aqueous solutions for enteral, parenteral or transmucosal administration, e.g., for intravenous administration, as tonics and administration to mucous or other membranes as, for example, nose or eye drops; solid and other non-aqueous compositions for enteral or transdermal delivery, e.g., as pills, tablets, powders or capsules; transdermal or transmucosal delivery systems for topical administration, and aerosols or mists for delivery by inhalation. One advantage of delivery by a mode that is easy to administer, e.g., enteral or by intravenous or intramuscular injection is that such modes mimic possible modes of delivery should the agent be formulated as a pharmaceutical.

In one embodiment, the pharmaceutical composition is in the form of a unit dose which contains a pharmacologically effective amount of the Repro-EN-1.0 or IB1 inhibitory compound. The unit dose, taken as part of a therapeutic regimen, results in inhibition of growth of prostate cancer cells. Thus, the pharmaceutical compositions of the invention, whatever the form, are administered in a pharmacologically effective amount to the subject.

The amount of the pharmaceutical composition delivered, the mode of administration and the time course of treatment are at the discretion of the treating physician. Prophylactic treatments are indicated for persons at higher than average risk of getting prostate cancer, breast cancer or uterine cancer. For example, persons with elevated PSA, PAP (prostate acid phosphatase) or PSP (prostate specific protein) levels are at increased risk of prostate cancer. Persons who have the BRCA1 or BRCA2 genes are at increased risk of breast cancer.

XII. Methods of Inhibiting an Immune Response Against Repro-EN-1.0 or IB1

Women with endometriosis exhibit auto-antibodies against Repro-EN-1.0. or IB1. This fact supports the idea that endometriosis involves an auto-immune response. Thus, this invention provides methods useful for inhibiting an immune response against Repro-EN-1.0 or IB1. In one embodiment, the methods include suppressing the immune system in persons with endometriosis. This includes, for example, the administration of immunosuppressive drugs such as anti-histamines, anti-inflammatories such as steroids, or cyclosporin or anti-idiotypic antibodies that recognize auto-antibodies against Repro-EN-1.0 or IB31.

In one embodiment of the invention, the immune response can be diminished by the eliciting in the subject anti-idiotypic antibodies against auto-antibodies that specifically recognize Repro-EN-1.0 or IB1. Anti-idiotypic antibodies are produced by immunizing the subject with antibodies against Repro-EN-1.0 or IB1. The amount of delivery to elicit an immune response can be about 1 µg to about 500 µg given with one or more booster administrations over about six weeks. Anti-idiotypic antibodies bind to the antigen binding site of the Repro-EN-1.0 or IB1 antibodies, thereby blocking their function.

In another embodiment of the invention the method involves inducing anergy in T cells involved in a humoral or cell-mediated immune response against Repro-EN-1.0 or IB1. Anergy can be induced by administering to a subject an MHC-peptide complex that comprises an MHC molecule coupled to a peptide epitope from Repro-EN-1.0 or IB1.

MHC Class I and MHC Class II molecules bind peptides having particular amino acid motifs in binding pockets located at the amino-terminus of the molecules. The MHC Class II molecule is a dimer formed from an alpha and a beta chain. The binding pocket is formed from portions of both chains. However, a single beta chain suffices to bind a peptide having the appropriate amino acid motif.

MHC-peptide complexes are formed by contacting a peptide having the appropriate motif with an isolated MHC Class II molecule. Alternatively, the complexes can be formed by creating fusion proteins containing both the MHC molecule and the polypeptide epitope.

Methods of inducing anergy involve administering an isolated MHC-peptide complex to an individual suffering from the auto-immune disease. Isolated complexes are complexes that do not exist anchored onto a cell surface. MHC-peptide complexes and methods of using them to induce anergy are described in, for example, U.S. Pat. Nos. 5,468,481 (S. D. Sharma et al.) and 5,734,023 (B. Nag et al.).

MHC Class II molecules bind peptides having particular amino acid motifs well known in the art. HLA-A1 binding motif includes a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues. A second motif consists of a first conserved residue of E or D and a second conserved residue of Y where the first and second conserved residues are separated by 5 to 6 residues. The HLA-A3.2 binding motif includes a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues. The HLA-A11 binding motif includes a first conserved residue of T or V at position 2 and a C-terminal conserved residue of K. The first and second conserved residues are preferably separated by 6 or 7 residues. The HLA-A24.1 binding motif includes a first conserved residue of Y, F or W at position 2 and a C terminal conserved residue of F, I, W, M or L. The first and second conserved residues are preferably separated by 6 to 7 residues.

This invention also provides a peptide comprising a linear epitope derived from the Repro-EN-1.0 or IB1 which specifically binds to an MHC molecule. In certain embodiments, the peptide has between 8 and 12 amino acids and the linear epitope has a Class I MHC molecule binding motif.

The following chart provides portions of the amino acid sequence of Repro-EN-1.0 (SEQ ID NO:2). Amino acid numbers are indicated. Bracketed bars over the amino acid sequence indicate vertebrate MHC Class I or MHC Class II binding motifs. Amino acid numbers are indicated. Peptides of about 8-15 amino acids in length that include these motifs, including peptides whose entire amino acid sequence is selected from the sequence of Repro-EN-1.0, bind to MHC molecules and can be used to induce a cell-mediated or humoral immune response against Repro-EN-1.0. Most of the sequence of Repro-EN-1.0 is exposed on the protein surface and is capable of eliciting an immune response.

This invention also provides a pharmaceutical composition capable of inducing anergy against Repro-EN-1.0 comprising a pharmaceutically acceptable carrier and an effective amount of an MHC-peptide complex of this invention. The complex is capable of inducing anergy in Class I MHC-restricted cytotoxic T-lymphocytes or Class II MHC-restricted immune response against cells expressing Repro-EN-1.0.

Repro-EN-1.0 includes many amino acid binding motifs for MHC Class I and MHC Class II. These motifs are provided in Table 1. The amino acid sequence numbers are provided and the motifs are indicated with bars.

TABLE 1

| | | |
|---|---|---|
| 337 | pnvslmqrmsdmlsrwfeeasevaqsnrgrgrsrp<br>347 350    358 361<br>351 354 | (SEQ ID NO: 11) |
| 386 | vpsspdlevsetamevdtpaeqflq<br>396 399 | (SEQ ID NO: 12) |
| 475 | pvlslhystegtttstiklnftdew<br>485 489 | (SEQ ID NO: 13) |
| 536 | etkapeessedvtkyqegvsaenp<br>546 549 | (SEQ ID NO: 14) |

TABLE 1-continued

```
           |--|
561  enhinitqsdkftakpldsnsgern                                        (SEQ ID NO: 15)
         571 574
           |--|
624  ntnpepqfqteatgpsaheetstr                                         (SEQ ID NO: 16)
         634 636
       |--|          |--|    |----|      |---|
675  drrsavariqeffrrrkerkemeeldtlnirrplvkmvykghrnsrtmikeanfwganfv      (SEQ ID NO: 17)
     685 688        700 703  710   714   720 724
       |--|          |---|
739  dcghifiwdrhtaehlmlleadnhvvnclqphpfdpi                             (SEQ ID NO: 18)
         749 752    762 765
       |---|    |--||--||---||---|              |---|
776  lassgidydikiwspleesrifnrkladevitrnelmleetrntitvpasfmlrmlasln      (SEQ ID NO: 19)
     786 789  795 798  804 808                 829 833
              800 803      810 814
       |---|
850  sgqenenedee                                                      (SEQ ID NO: 20)
     855 858
```

XIII. Transgenic Non-Human Animals

This invention also provides non-human mammals transgenic for Repro-EN-1.0 and IB1. As used herein, "animal transgenic for Repro-EN-1.0 or IB1" refers to an animal, in particular a mammal, whose germ cells (i.e., oocytes or sperm), at least, comprise a recombinant nucleic acid molecule comprising expression control sequences operatively linked to a nucleic acid sequence encoding Repro-EN-1.0 or IB1. Such animals are useful, for example, as models in the study of endometriosis, spontaneous abortion and disease pathways.

In one embodiment, the expression control sequences are not naturally found operatively linked to Repro-EN-1.0. In one embodiment, the recombinant nucleic acid comprises a non-native Repro-EN-1.0 coding sequence, i.e., a Repro-EN-1.0 sequence that the species does not produce in nature. In one embodiment, the Repro-EN-1.0 is a human Repro-EN-1.0. In another embodiment, the expression control sequences are non-native expression control sequences introduced into the germ cells so as to recombine with the naturally occurring gene and control its expression. Particularly useful transgenic mammals of this invention include rabbits and rodents such as mice.

The transgenic animals of this invention are produced, for example, by introducing the recombinant nucleic acid molecule into a fertilized egg or embryonic stem (ES) cell, typically by microinjection, electroporation, lipofection, particle-mediated gene transfer. The transgenic animals express the heterologous nucleotide sequence in tissues depending upon whether the promoter is inducible by a signal to the cell, or is constitutive. Transgenic animals can be bred with non-transgenic animals to produce transgenic animals with mixed characteristics.

XIV. Methods for Screening for Compounds that Regulate Expression of Repro-EN-1.0 or IB1

Compounds that regulate the expression of Repro-EN-1.0 and IB1 are candidates as therapeutic agents in the treatment of breast, uterine or prostate cancer. This invention provides methods for determining whether a compound regulates (e.g., activates or inhibits) expression of Repro-EN-1.0 or IB1.

Methods for determining whether a compound regulates Repro-EN-1.0 or IB1 expression involve administering to a cell or a test animal having an expressible Repro-EN-1.0 or IB1 gene with the compound, and determining whether expression Repro-EN-1.0 or IB1 is altered. In one embodiment, the methods involve administering the compound to a culture comprising the cell or to a test animal that has cells expressing Repro-EN-1.0 or IB1, measuring the amount of the Repro-EN-1.0 or IB1 polynucleotide or polypeptide in a sample from the culture or the animal, and determining whether the measured amount is different than the amount in a sample from the culture or from the animal under control conditions (e.g., to which no compound has been administered). Statistically significant ($p<0.05$) differences between the amount measured from the test sample and from the control sample are recorded and indicate that the compound alters the amount of Repro-EN-1.0 or IB1 produced by the cell.

The compound to be tested can be selected from a number of sources. For example, combinatorial libraries of molecules are available for screening experiments. Using such libraries, thousands of molecules can be screened for regulatory activity. In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487-493, Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc.*

Nat. Acad. Sci. USA 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

In one embodiment this invention provides inhibitory compounds that inhibit expression of Repro-EN-1.0 or IB1 identified or identifiable by the screening methods of this invention.

XV. Genomics

The identification of cognate or polymorphic forms of the Repro-EN-1.0 or IB1 gene and the tracking of those polymorphisms in individuals and families is important in genetic screening. Accordingly, this invention provides methods useful in detecting polymorphic forms of the Repro-EN-1.0 or IB1 gene. The methods involve comparing the identity of a nucleotide or amino acid at a selected position within the sequence of a test Repro-EN-1.0 or IB1 gene with the nucleotide or amino acid at the corresponding position from the sequence of native Repro-EN-1.0 (SEQ ID NO: 1) or IB1 (SEQ ID NO:3). The comparison can be carried out by any methods known in the art, including direct sequence comparison by nucleotide sequencing, sequence comparison or determination by hybridization or identification of RFLPs.

In one embodiment, the method involves nucleotide or amino acid sequencing of the entire test polynucleotide or polypeptide, or a subsequence from it, and comparing that sequence with the sequence of native Repro-EN-1.0 or IB1. In another embodiment, the method involves identifying restriction fragments produced upon restriction enzyme digestion of the test polynucleotide and comparing those fragments with fragments produced by restriction enzyme digestion of native Repro-EN-1.0 or IB1 gene. Restriction fragments from the native gene can be identified by analysis of the sequence to identify restriction sites. Another embodiment involves the use of oligonucleotide arrays. (See, e.g., Fodor et al., U.S. Pat. No. 5,445,934.) The method involves providing an oligonucleotide array comprising a set of oligonucleotide probes that define sequences selected from the native Repro-EN-1.0 or IB1 sequence, generating hybridization data by performing a hybridization reaction between the target polynucleotide molecules and the probes in the set and detecting hybridization between the target molecules and each of the probes in the set and processing the hybridization data to determine nucleotide positions at which the identity of the target molecule differs from that of native Repro-EN-1.0 or IB1. The comparison can be done manually, but is more conveniently done by a programmable, digital computer.

The following examples are offered by way of illustration, not by way of limitation.

EXAMPLES

I. Construction of a Human Endometrial Carcinoma Cell Line (RL95-2) cDNA Expression Library A. Material and Methods Poly A+ RNA isolated from RL95-2, was used as a template for first strand cDNA synthesis. The poly A+ RNA was analyzed by denaturing gel electrophoresis and ranged in size from 0.2 to 10 Kb (10). An oligo dT primer containing an internal, protected XhoI site was annealed in the presence of a nucleotide mixture containing 5-methyl dCTP, and extended with MMTV reverse transcriptase.

Second strand synthesis of the RL95-2 cDNA/RNA hybrid was completed by the addition of RNase H, DNA polymerase 1, and dNTPs to the first strand synthesis reaction. Pfu DNA polymerase was used to blunt-end the double stranded RL95-2 cDNA followed by the ligation of EcoRI adapters. The cDNA was kinased and digested with XhoI and EcoRI before size fractionation on Sephacryl S-500 columns. The size fractionated cDNA was recovered and the quantified on ethidium bromide containing plates against a set of serially-diluted DNA standards. The cDNA contained in the first two column fractionations was directionally ligated, in the sense orientation, to XhoI/EcoRI-digested uniZAP phage vector arms. Initially, approximately 25 ng (per fraction) of the cDNA was ligated and packaged into bacteriophage particles. Subsequently, the approximately 100 ng remaining cDNA in fractions 1 and 2 was packaged into bacteriophage particles using several reactions of the lambda phage packaging extract (Stratagene).

After packaging, the primary human RL95-2 library was titered by infection of the XL1 Blue host strain. The ratio of recombinant:nonrecombinant phage was determined by plating infected XL1 Blue in the presence of IPTG and XGal. The number of blue (non-recombinant) or white (recombinant) plaques were quantified using a Manostat colony counter. Ninety-eight and one-half (98.5) percent of the phage in the human RL95-2 cDNA library were recombinant and the primary phage library base consisted of $2.2 \times 10^6$ independent clones. The human RL95-2 cDNA library was amplified once and re-titered as above. The titer of the amplified library was $3 \times 10^9$ pfu/ml.

The average size of the cDNA inserts was determined by PCR amplification. Twenty well-isolated phage plaques were cored and the cDNA inserts were amplified using T7/T3 specific oligonucleotides which hybridize to sites flanking the cDNA insertion site contained within the lambda phage vector. The PCR products were analyzed by agarose gel electrophoresis and visualized by ethidium bromide staining. Ninety-five percent of the cored plaques contained inserts varying in size from 0.5 to 2.5 Kb with an average size of 1.5 Kb.

II. Library Screening

To identify endometrial autoantigens that could be used to develop an endometriosis immunoassay, pooled sera from patients (n=17) with laparoscopy confirmed endometriosis was used as a probe to screen the RL95-2 cDNA expression library using the following methods.

A. Preadsorption of serum. Antibodies that react with expression library host strains were immunoadsorbed from patient serum by using BNN97 and Y1090 E. coli lysate-conjugated sepharose beads (5'→3') following the manufacturer's protocols. Briefly, 2 ml of host stain lysate-conjugated sepharose beads were washed twice with sterile Tris buffered saline (TBS). The beads were resuspended in 4 mls of serum diluted 1/2 in TBS. Following a 16 hour incubation at 4° C., the sepharose beads were collected by centrifugation at 1,000×g for 2 min. The supernatant was removed and the beads were washed with 4 mls of sterile TBS. After centrifugation at 1,000×g for 2 min, the supernatants were collected, pooled and used to screen the RL95-2-specific cDNA expression library.

B Screening the RL95-2 cDNA library. Approximately $10^6$ infectious phage particles were incubated with XL-1 blue host cells and plated at density of 50,000 phage per 150 mm dish using standard protocols (Stratagene). After incubating for 5 hours at 42° C., the phage plaques were overlaid with nitrocellulose membranes (Protran; Schleicher & Schuell) that had been soaked in a 10 mM isopropyl-1-thio-b-D-galactopyranoside (IPTG) solution. Following a 4 hour incubation at 37° C., the membranes were removed and washed three times for 15 min in TBS with 0.05% Tween$_{20}$ (TTBS). The membranes were incubated with blocking solution (1% Bovine serum albumin [fraction V] in TBS) for 1 hour at room temperature prior to a 1 hour incubation with preadsorbed patient serum diluted 1/10 (final dilution of 1/40) in blocking solution. The membranes were washed three time for 15 min with TTBS prior to the addition of alkaline phosphatase-conjugated goat anti-human Ig(G,A,M) (Pierce) diluted 1/25,000 in blocking solution. After a 1 hour incubation at room temperature the membranes were washed three times with TTBS as described above and once with TBS. The membranes were incubated with enzyme substrate (Western Blue; Promega) for approximately 30 min and the enzymatic reaction was terminated by briefly incubating the membranes with stop solution (Tris-HCl pH 2.9; 1 mM EDTA). Several immunoreactive phage plaques were selected and transferred to 500 µl of SM buffer (100 mM NaCl, 8 mM MgSO$_4$, 50 mM Tris-HCl pH 7.5, 0.01% gelatin) containing 20 µl of chloroform. The selected phage were eluted from the agar and plated at a density of approximately 1,000 phage per 100 mm dish and screen as described above. To insure that the selected phage plaque, named Repro-EN-1.0, represented a single clone the screening process was repeated a third time as described above.

C. Excision of Repro-EN-1.0 phagemid. Plasmid containing the cDNA insert for Repro-EN-1.0 was excised from the phage clone using the manufacturer's protocols (Stratagene). The size of the Repro-EN-1.0 insert was determined by releasing the cDNA fragment from the rescued pBluescript/Repro-EN-1.0 plasmid with the restriction enzymes EcoRl and Xhol. The released insert was size fractionated by agarose-gel electrophoresis and the apparent length of the insert was determined by comparing its migration position with a DNA standard (1 kb ladder; Gibco BRL). The insert migrated at approximately 2.0 Kb.

D. Identification of the IB1 clone. An alternately spliced variant of Repro-EN-1.0. A commercial human heart cDNA library (Clontech) was screened with a radiolabeled probe mapping within the amino terminus of the Repro-EN-1.0 coding sequence (nt 203 to 897). One of the two clones isolated contained a cDNA insert of 3.4 Kb which possessed an extra 231 base pair insert within the Repro-EN-1.0 coding sequence.

III. Characterization

A. Sequence analysis

The nucleotide sequence of Repro-EN-1.0 was determined by using a modified protocol of the dideoxy chain termination method of Sanger et al. and USB Sequenase 2.0 (Barker, D. F. 1993, *Biotechniques*). The amino acid sequence was predicted using the Intelligenetic TRANSLATE program and sequence homologies were determined with BLAST data base search algorithms. The deduced amino acid sequence (in the expected frame for a fusion protein) was novel.

B. Tissue Expression Analysis

Figure 2:
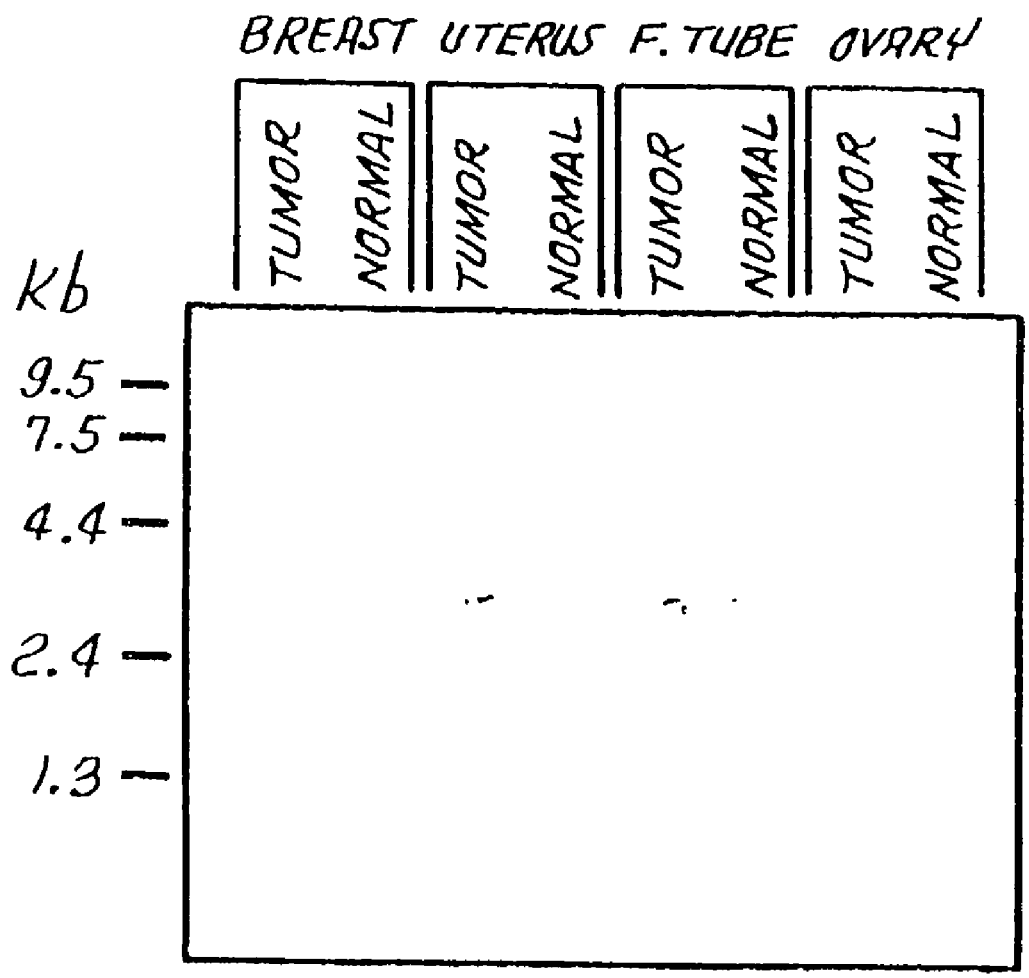
FIG. 2 is a northern blot analysis of Repro-EN-1.0 expression comparing various normal v. cancerous tissues.
Figure 3:
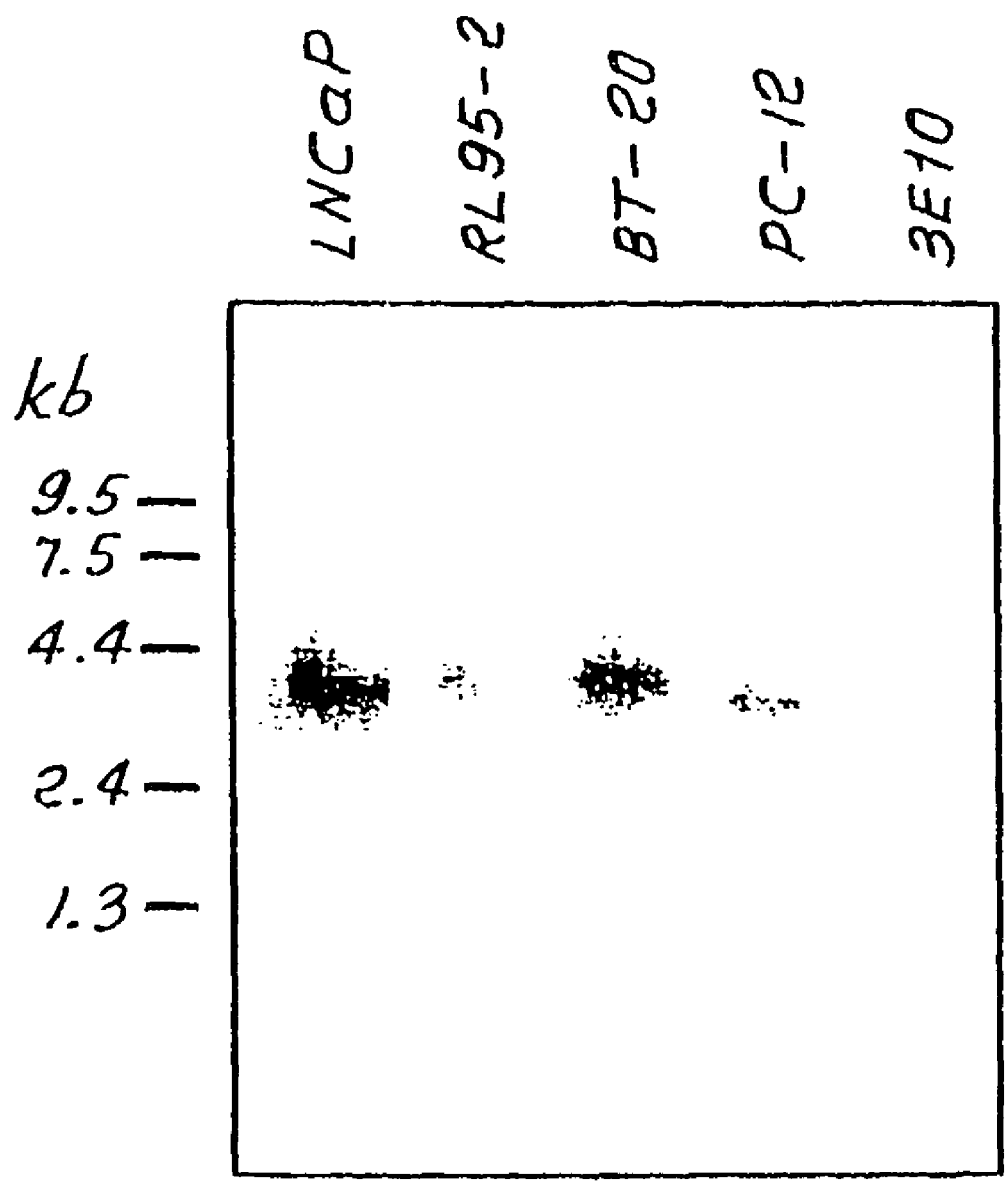
FIG. 3 is a northern blot analysis of Repro-EN-1.0 expression in various tissue culture cells.

The Repro-EN-1.0 expression distribution was determined by Northern blot analysis using poly A+ RNA collected from human spleen, thymus, prostate, testis, ovary, small intestine, colon, and peripheral blood leukocytes (MTN human blot 11; Clontech) and human heart, brain, placenta, lung, liver, skeletal muscle, kidney and pancreas (MTN human blot 1-Clontech) and the manufacturer' suggested protocols (Clontech). The immobilized poly A+ RNA samples were incubated with a random prime labeled probe that represented the Repro-EN-1.0 insert. The probe was generated by using and EcoRl/Xhol released fragment of pRepro-EN-1.0 as template for a random prime labeled reaction as described in the manufacturer's manual (Megaprime kit; Amersham). The Northern blot membranes were prehybridized with 6 mls of ExpressHyb solution (Clontech) followed by a 1 hour incubation at 68° C. with approximately 0.5 ng of radiolabeled probe (approx. 2×105 cpm) in 5 mls of ExpressHyb solution. Unbound probe was removed by washing the membranes three times with 2×SSC, 0.05% SDS at room temperature for 10 min for each wash followed by twice with 0.1×SSC, 0.1% SDS at 50° C. for 15 min for each wash. The apparent length of RNA species, a 3.4 Kb mRNA, and tissue distribution was determined by autoradiography. Expression was detected primarily in skeletal muscle, heart and testis; and to a lesser extent in other tissues, but was not detected in lung or peripheral blood mononuclear cells (PBMC). Expression of Repro-EN-1.0 was up-regulated in breast and uterine carcinomas relative to their normal counterparts, was highly expressed in both normal fallopian tube and fallopian tube carcinoma, and was expressed at low levels in both normal ovary and ovarian carcinoma (FIG. 2 and FIG. 3). Expression of Repro-EN-1.0 in RL95-2 (endometrium carcinoma) cells is lower than in LNCaP (human prostate adenocarcinoma), PC-12 (rat cell line) and BT12 (human breast carcinoma cell line) cells and undetectable in a mouse hybridoma cell line (3E10; negative control) (FIG. 4). In addition, expression in normal endometrium is undetectable.

C. Homologue Analysis

To determine the level of nucleotide conservation of Repro-EN-1.0 in different species, a Southern blot analysis using EcoRl digested genomic DNA collected from human, monkey, rat, mouse, dog, cow, rabbit, chicken and yeast was performed as described in the manufacture's manual (ZooBlot; Clontech). Briefly, the immobilized EcoRl digested genomic DNA samples were prehybridized with 6 mls of ExpressHyb (Clontech) and incubated for 1 hour at 68° C. with 1.0 ng (approx. 4×10$^5$ cpm in 5 mls) of a random prime labeled probe that represented the Repro-EN-1.0 insert. Unbound probe was removed by washing the membranes once with 2×SSC, 0.05% SDS at room temperature for 30 min followed by one wash with 0.1×SSC, 0.1% SDS at 50 C for 30 min. Identification of homologues in different species was determine by autoradiography. (See FIG. 4) The sequence is highly conserved between human and non-human primates (Monkey).

IV. Antibodies

Antibodies to peptides of the clone and/or to recombinant protein were generated in rabbits. This antisera was used to develop a Repro-EN-1.0 ELISA.

V. Recombinant Protein

The predicted ORF for Repro-EN-1 was subcloned into an expression vector, and the recombinant protein was expressed and purified by Ni-Chelate chromatography using standard methodologies.

VI. ELISA

The purified recombinant Repro-EN-1 protein was used as a target antigen in an ELISA (EndX™ ELISA) designed to detect antigen-specific autoantibodies in patient serum.

The present invention provides a novel nucleotide sequence encoding Repro-EN-1.0, Repro-EN-1.0 polypeptides, IB1, IB1 polypeptides and methods of using these materials. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method for diagnosing endometriosis in a human subject comprising the steps of:
   (a) detecting a test amount of an antibody that specifically binds to SEQ ID NO: 2 or SEQ ID NO: 4 polypeptide or a truncated peptide comprising an epitope of SEQ ID NO: 2 or SEQ ID NO: 4 polypeptide, in a sample from the subject; and
   (b) comparing the test amount with a normal range of the antibody in a control sample from a subject who does not suffer from endometriosis, whereby a test amount above the normal range of the antibody provides a positive indication in the diagnosis of endometriosis.

2. The method of claim 1, wherein the sample comprises blood serum, peritoneal fluid, menstrual fluid, vaginal secretion or urine.

3. The method of claim 1 or 2, wherein the step of detecting comprises capturing the antibody from the sample with said polypeptide or peptide which has been immobilized and detecting captured antibody.

4. The method of claim 1 wherein said polypeptide has the amino acid sequence identical to SEQ ID NO:2.

5. The method of claim 1 wherein said polypeptide has the amino acid sequence identical to SEQ ID NO: 4.

6. The method of claim 1 wherein said truncated peptide comprises an epitope of SEQ ID NO: 2.

7. The method of claim 1 wherein said truncated peptide comprises an epitope of SEQ ID NO: 4.

8. The method of claim 1 wherein said SEQ ID NO: 2 or SEQ ID NO: 4 polypeptide is produced by recombinant means.

9. The method of claim 1 wherein said truncated peptide of SEQ ID NO: 2 or SEQ ID NO: 4 is produced by recombinant means.

* * * * *

```
                          SEQUENCE LISTING

<160> NUMBER OF SEQ ID NOS: 20

<210> SEQ ID NO 1
<211> LENGTH: 3189
<212> TYPE: DNA
<213> ORGANISM: Homo sapiens
<220> FEATURE:
<221> NAME/KEY: CDS
<222> LOCATION: (176)..(2755)

<400> SEQUENCE: 1
cggccgggct tcaggggccc aggcgccgct gctgccaccg ccatctaacg ctgcgccctg       60
gaggcccggc gcgcggatgg tgccggtgcg gctcgggtgt tgaaacgggt gtcccctccc      120
cctcctcccc tccccacgc ggtggtctcc cctcccaccc ggctcaggca gagcc atg       178
                                                              Met
                                                               1 tct cgg ggt ggc tcc tac cca cac ctg ttg tgg gac gtg agg aaa agg        226
Ser Arg Gly Gly Ser Tyr Pro His Leu Leu Trp Asp Val Arg Lys Arg
            5                  10                  15 ttc ctc ggg ctg gag gac ccg tcc cgg ctg cgg agt cgc tac ctg gga        274
Phe Leu Gly Leu Glu Asp Pro Ser Arg Leu Arg Ser Arg Tyr Leu Gly
         20                  25                  30 aga aga gaa ttt atc caa aga tta aaa ctt gaa gca acc ctt aat gtg        322
Arg Arg Glu Phe Ile Gln Arg Leu Lys Leu Glu Ala Thr Leu Asn Val
     35                  40                  45 cat gat ggt tgt gtt aat aca atc tgt tgg aat gac act gga gaa tat        370
His Asp Gly Cys Val Asn Thr Ile Cys Trp Asn Asp Thr Gly Glu Tyr
 50                  55                  60                  65 att tta tct ggc tca gat gac acc aaa tta gta att agt aat cct tac        418
Ile Leu Ser Gly Ser Asp Asp Thr Lys Leu Val Ile Ser Asn Pro Tyr
                 70                  75                  80 agc aga aag gtt ttg aca aca att cgt tca ggg cac cga gca aac ata        466
Ser Arg Lys Val Leu Thr Thr Ile Arg Ser Gly His Arg Ala Asn Ile
             85                  90                  95 ttt agt gca aag ttc tta cct tgt aca aat gat aaa cag att gta tcc        514
Phe Ser Ala Lys Phe Leu Pro Cys Thr Asn Asp Lys Gln Ile Val Ser
            100                 105                 110
```

-continued

| | |
|---|---|
| tgc tct gga gat gga gta ata ttt tat acc aac gtt gag caa gat gca<br>Cys Ser Gly Asp Gly Val Ile Phe Tyr Thr Asn Val Glu Gln Asp Ala<br>115                     120                    125 | 562 |
| gaa acc aac aga caa tgc caa ttt acg tgt cat tat gga act act tat<br>Glu Thr Asn Arg Gln Cys Gln Phe Thr Cys His Tyr Gly Thr Thr Tyr<br>130                 135                  140                145 | 610 |
| gag att atg act gta ccc aat gac cct tac act ttt ctc tct tgt ggt<br>Glu Ile Met Thr Val Pro Asn Asp Pro Tyr Thr Phe Leu Ser Cys Gly<br>                    150                  155                  160 | 658 |
| gaa gat gga act gtt agg tgg ttt gat aca cgc atc aaa act agc tgc<br>Glu Asp Gly Thr Val Arg Trp Phe Asp Thr Arg Ile Lys Thr Ser Cys<br>                165                  170                175 | 706 |
| aca aaa gaa gat tgt aaa gat gat att tta att aac tgt cga cgt gct<br>Thr Lys Glu Asp Cys Lys Asp Asp Ile Leu Ile Asn Cys Arg Arg Ala<br>180                     185                  190 | 754 |
| gcc acg tct gtt gct att tgc cca cca ata cca tat tac ctt gct gtt<br>Ala Thr Ser Val Ala Ile Cys Pro Pro Ile Pro Tyr Tyr Leu Ala Val<br>195                     200                  205 | 802 |
| ggt tgt tct gac agc tca gta cga ata tat gat cgg cga atg ctg ggc<br>Gly Cys Ser Asp Ser Ser Val Arg Ile Tyr Asp Arg Arg Met Leu Gly<br>210                     215                  220                225 | 850 |
| aca aga gct aca ggg aat tat gca ggt cga ggg act act gga atg gtt<br>Thr Arg Ala Thr Gly Asn Tyr Ala Gly Arg Gly Thr Thr Gly Met Val<br>                    230                  235                  240 | 898 |
| gcc cgt ttt att cct tcc cat ctt aat aat aag tcc tgc aga gtg aca<br>Ala Arg Phe Ile Pro Ser His Leu Asn Asn Lys Ser Cys Arg Val Thr<br>                245                  250                255 | 946 |
| tct ctg tgt tac agt gaa gat ggt caa gag att ctc gtt agt tac tct<br>Ser Leu Cys Tyr Ser Glu Asp Gly Gln Glu Ile Leu Val Ser Tyr Ser<br>260                     265                  270 | 994 |
| tca gat tac ata tat ctt ttt gac ccg aaa gat gat aca gca cga gaa<br>Ser Asp Tyr Ile Tyr Leu Phe Asp Pro Lys Asp Asp Thr Ala Arg Glu<br>275                     280                  285 | 1042 |
| ctt aaa act cct tct gcg gaa gag aga aga gaa gag ttg cga caa cca<br>Leu Lys Thr Pro Ser Ala Glu Glu Arg Arg Glu Glu Leu Arg Gln Pro<br>290                     295                  300                305 | 1090 |
| cca gtt aag cgt ttg aga ctt cgt ggt gat tgg tca gat act gga ccc<br>Pro Val Lys Arg Leu Arg Leu Arg Gly Asp Trp Ser Asp Thr Gly Pro<br>                310                  315                320 | 1138 |
| aga gca agg ccg gag agt gaa cga gaa cga gat gga gag cag agt ccc<br>Arg Ala Arg Pro Glu Ser Glu Arg Glu Arg Asp Gly Glu Gln Ser Pro<br>                    325                  330                335 | 1186 |
| aat gtg tca ttg atg cag aga atg tct gat atg tta tca aga tgg ttt<br>Asn Val Ser Leu Met Gln Arg Met Ser Asp Met Leu Ser Arg Trp Phe<br>                340                  345                350 | 1234 |
| gaa gaa gca agt gag gtt gca caa agc aat aga gga cga gga aga tct<br>Glu Glu Ala Ser Glu Val Ala Gln Ser Asn Arg Gly Arg Gly Arg Ser<br>355                     360                  365 | 1282 |
| cga ccc aga ggt gga aca agt caa tca gat att tca act ctt cct acg<br>Arg Pro Arg Gly Gly Thr Ser Gln Ser Asp Ile Ser Thr Leu Pro Thr<br>370                     375                  380                385 | 1330 |
| gtc cca tca agt cct gat ttg gaa gtg agt gaa act gca atg gaa gta<br>Val Pro Ser Ser Pro Asp Leu Glu Val Ser Glu Thr Ala Met Glu Val<br>                    390                  395                  400 | 1378 |
| gat act cca gct gaa caa ttt ctt cag cct tct aca tcc tct aca atg<br>Asp Thr Pro Ala Glu Gln Phe Leu Gln Pro Ser Thr Ser Ser Thr Met<br>                405                  410                415 | 1426 |
| tca gct cag gct cat tcg aca tca tct ccc aca gaa agc cct cat tct<br>Ser Ala Gln Ala His Ser Thr Ser Ser Pro Thr Glu Ser Pro His Ser<br>420                     425                  430 | 1474 |

-continued

| | | |
|---|---|---|
| act cct ttg cta tct tct cca gat agt gaa caa agg cag tct gtt gag<br>Thr Pro Leu Leu Ser Ser Pro Asp Ser Glu Gln Arg Gln Ser Val Glu<br>435                    440                    445 | | 1522 |
| gca tct gga cac cac aca cat cat cag tct gat aac aat aat gaa aag<br>Ala Ser Gly His His Thr His His Gln Ser Asp Asn Asn Asn Glu Lys<br>450                    455                    460                    465 | | 1570 |
| ctg agc ccc aaa cca ggg aca ggt gaa cca gtt tta agt ttg cac tac<br>Leu Ser Pro Lys Pro Gly Thr Gly Glu Pro Val Leu Ser Leu His Tyr<br>                    470                    475                    480 | | 1618 |
| agc aca gaa gga aca act aca agc aca ata aaa ctg aac ttt aca gat<br>Ser Thr Glu Gly Thr Thr Thr Ser Thr Ile Lys Leu Asn Phe Thr Asp<br>                485                    490                    495 | | 1666 |
| gaa tgg agc agt ata gca tca agt tct aga gga att ggg agc cat tgc<br>Glu Trp Ser Ser Ile Ala Ser Ser Arg Gly Ile Gly Ser His Cys<br>        500                    505                    510 | | 1714 |
| aaa tct gag ggt cag gag gaa tct ttc gtc cca cag agc tca gtg caa<br>Lys Ser Glu Gly Gln Glu Glu Ser Phe Val Pro Gln Ser Ser Val Gln<br>515                    520                    525 | | 1762 |
| cca cca gaa gga gac agt gaa aca aaa gct cct gaa gaa tca tca gag<br>Pro Pro Glu Gly Asp Ser Glu Thr Lys Ala Pro Glu Glu Ser Ser Glu<br>530                    535                    540                    545 | | 1810 |
| gat gtg aca aaa tat cag gaa gga gta tct gca gaa aac cca gtt gag<br>Asp Val Thr Lys Tyr Gln Glu Gly Val Ser Ala Glu Asn Pro Val Glu<br>                    550                    555                    560 | | 1858 |
| aac cat atc aat ata aca caa tca gat aag ttc aca gcc aag cca ttg<br>Asn His Ile Asn Ile Thr Gln Ser Asp Lys Phe Thr Ala Lys Pro Leu<br>                565                    570                    575 | | 1906 |
| gat tcc aac tca gga gaa aga aat gac ctc aat ctt gat cgc tct tgt<br>Asp Ser Asn Ser Gly Glu Arg Asn Asp Leu Asn Leu Asp Arg Ser Cys<br>        580                    585                    590 | | 1954 |
| ggg gtt cca gaa gaa tct gct tca tct gaa aaa gcc aag gaa cca gaa<br>Gly Val Pro Glu Glu Ser Ala Ser Ser Glu Lys Ala Lys Glu Pro Glu<br>595                    600                    605 | | 2002 |
| act tca gat cag act agc act gag agt gct acc aat gaa aat aac acc<br>Thr Ser Asp Gln Thr Ser Thr Glu Ser Ala Thr Asn Glu Asn Asn Thr<br>610                    615                    620                    625 | | 2050 |
| aat cct gag cct cag ttc caa aca gaa gcc act ggg cct tca gct cat<br>Asn Pro Glu Pro Gln Phe Gln Thr Glu Ala Thr Gly Pro Ser Ala His<br>                    630                    635                    640 | | 2098 |
| gaa gaa aca tcc acc agg gac tct gct ctt cag gac aca gat gac agt<br>Glu Glu Thr Ser Thr Arg Asp Ser Ala Leu Gln Asp Thr Asp Asp Ser<br>                645                    650                    655 | | 2146 |
| gat gat gac cca gtc ctg atc cca ggt gca agg tat cga gca gga cct<br>Asp Asp Asp Pro Val Leu Ile Pro Gly Ala Arg Tyr Arg Ala Gly Pro<br>        660                    665                    670 | | 2194 |
| ggt gat aga cgc tct gct gtt gcc cgt att cag gag ttc ttc aga cgg<br>Gly Asp Arg Arg Ser Ala Val Ala Arg Ile Gln Glu Phe Phe Arg Arg<br>675                    680                    685 | | 2242 |
| aga aaa gaa agg aaa gaa atg gaa gaa ttg gat act ttg aac att aga<br>Arg Lys Glu Arg Lys Glu Met Glu Glu Leu Asp Thr Leu Asn Ile Arg<br>690                    695                    700                    705 | | 2290 |
| agg ccg cta gta aaa atg gtt tat aaa ggc cat cgc aac tcc agg aca<br>Arg Pro Leu Val Lys Met Val Tyr Lys Gly His Arg Asn Ser Arg Thr<br>                    710                    715                    720 | | 2338 |
| atg ata aaa gaa gcc aat ttc tgg ggt gct aac ttt gta atg act ggt<br>Met Ile Lys Glu Ala Asn Phe Trp Gly Ala Asn Phe Val Met Thr Gly<br>                725                    730                    735 | | 2386 |
| tct gag tgt ggc cac att ttc atc tgg gat cgg cac act gct gag cat<br>Ser Glu Cys Gly His Ile Phe Ile Trp Asp Arg His Thr Ala Glu His | | 2434 |

-continued

```
                  740                 745                 750
ttg atg ctt ctg gaa gct gat aat cat gtg gta aac tgc ctg cag cca    2482
Leu Met Leu Leu Glu Ala Asp Asn His Val Val Asn Cys Leu Gln Pro
    755                 760                 765 cat ccg ttt gac cca att tta gcc tca tct ggc ata gat tat gac ata    2530
His Pro Phe Asp Pro Ile Leu Ala Ser Ser Gly Ile Asp Tyr Asp Ile
770                 775                 780                 785 aag atc tgg tca cca tta gaa gag tca agg att ttt aac cga aaa ctt    2578
Lys Ile Trp Ser Pro Leu Glu Glu Ser Arg Ile Phe Asn Arg Lys Leu
                790                 795                 800 gct gat gaa gtt ata act cga aac gaa ctc atg ctg gaa gaa act aga    2626
Ala Asp Glu Val Ile Thr Arg Asn Glu Leu Met Leu Glu Glu Thr Arg
            805                 810                 815 aac acc att aca gtt cca gcc tct ttc atg ttg agg atg ttg gct tca    2674
Asn Thr Ile Thr Val Pro Ala Ser Phe Met Leu Arg Met Leu Ala Ser
        820                 825                 830 ctt aat cat atc cga gct gac cgg ttg gag ggt gac aga tca gaa ggc    2722
Leu Asn His Ile Arg Ala Asp Arg Leu Glu Gly Asp Arg Ser Glu Gly
    835                 840                 845 tct ggt caa gag aat gaa aat gag gat gag gaa taataaactc ttttggcaa    2775
Ser Gly Gln Glu Asn Glu Asn Glu Asp Glu Glu
850                 855                 860 gcacttaaat gttctgaaat ttgtataaga catttattat ttttttttct ttacagagat    2835
ttagtgcaat tttaaggtta tggttttttgg agtttttccc ttttttttggg ataacctaac    2895 attggtttgg aatgattgtg tgcatgaatt tgggagattg tataaaacaa aactagcaga    2955 atgttttttaa aacttttttgc cgtgtatgag gagtgctaga aaatgcaaag tgcaatattt    3015
tccctaacct tcaaatgtgg gagcttggat caatgttgaa gaataatttt catcatagtg    3075
aaaatgttgg ttcaaataaa tttctacact tgccatttgc atgtttgttg ctttctaatt    3135
aaagaaactg gttgttttaa gatacactga aaaaaaaaaa aaaaaaaaaa aaaa    3189
```

<210> SEQ ID NO 2
<211> LENGTH: 860
<212> TYPE: PRT
<213> ORGANISM: Homo sapiens

<400> SEQUENCE: 2

```
Met Ser Arg Gly Gly Ser Tyr Pro His Leu Leu Trp Asp Val Arg Lys
 1               5                  10                  15

Arg Phe Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
                85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140
```

-continued

```
Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Gly Thr Met
225                 230                 235                 240

Val Ala Arg Phe Ile Pro Ser His Leu Asn Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
                325                 330                 335

Pro Asn Val Ser Leu Met Gln Arg Met Ser Asp Met Leu Ser Arg Trp
            340                 345                 350

Phe Glu Glu Ala Ser Glu Val Ala Gln Ser Asn Arg Gly Arg Gly Arg
        355                 360                 365

Ser Arg Pro Arg Gly Gly Thr Ser Gln Ser Asp Ile Ser Thr Leu Pro
    370                 375                 380

Thr Val Pro Ser Ser Pro Asp Leu Glu Val Ser Glu Thr Ala Met Glu
385                 390                 395                 400

Val Asp Thr Pro Ala Glu Gln Phe Leu Gln Pro Ser Thr Ser Ser Thr
                405                 410                 415

Met Ser Ala Gln Ala His Ser Thr Ser Ser Pro Thr Glu Ser Pro His
            420                 425                 430

Ser Thr Pro Leu Leu Ser Ser Pro Asp Ser Glu Gln Arg Gln Ser Val
        435                 440                 445

Glu Ala Ser Gly His His Thr His His Gln Ser Asp Asn Asn Asn Glu
    450                 455                 460

Lys Leu Ser Pro Lys Pro Gly Thr Gly Glu Pro Val Leu Ser Leu His
465                 470                 475                 480

Tyr Ser Thr Glu Gly Thr Thr Thr Ser Thr Ile Lys Leu Asn Phe Thr
                485                 490                 495

Asp Glu Trp Ser Ser Ile Ala Ser Ser Arg Gly Ile Gly Ser His
            500                 505                 510

Cys Lys Ser Glu Gly Gln Glu Ser Phe Val Pro Gln Ser Ser Val
        515                 520                 525

Gln Pro Pro Glu Gly Asp Ser Thr Lys Ala Pro Glu Glu Ser Ser
    530                 535                 540

Glu Asp Val Thr Lys Tyr Gln Glu Gly Val Ser Ala Glu Asn Pro Val
545                 550                 555                 560

Glu Asn His Ile Asn Ile Thr Gln Ser Asp Lys Phe Thr Ala Lys Pro
```

```
                    565                 570                 575
Leu Asp Ser Asn Ser Gly Glu Arg Asn Asp Leu Asn Leu Asp Arg Ser
                580                 585                 590

Cys Gly Val Pro Glu Glu Ser Ala Ser Ser Glu Lys Ala Lys Glu Pro
            595                 600                 605

Glu Thr Ser Asp Gln Thr Ser Thr Glu Ser Ala Thr Asn Glu Asn Asn
        610                 615                 620

Thr Asn Pro Glu Pro Gln Phe Gln Thr Glu Ala Thr Gly Pro Ser Ala
625                 630                 635                 640

His Glu Glu Thr Ser Thr Arg Asp Ser Ala Leu Gln Asp Thr Asp Asp
                645                 650                 655

Ser Asp Asp Pro Val Leu Ile Pro Gly Ala Arg Tyr Arg Ala Gly
            660                 665                 670

Pro Gly Asp Arg Arg Ser Ala Val Ala Arg Ile Gln Glu Phe Phe Arg
        675                 680                 685

Arg Arg Lys Glu Arg Lys Glu Met Glu Glu Leu Asp Thr Leu Asn Ile
    690                 695                 700

Arg Arg Pro Leu Val Lys Met Val Tyr Lys Gly His Arg Asn Ser Arg
705                 710                 715                 720

Thr Met Ile Lys Glu Ala Asn Phe Trp Gly Ala Asn Phe Val Met Thr
                725                 730                 735

Gly Ser Glu Cys Gly His Ile Phe Ile Trp Asp Arg His Thr Ala Glu
            740                 745                 750

His Leu Met Leu Leu Glu Ala Asp Asn His Val Val Asn Cys Leu Gln
        755                 760                 765

Pro His Pro Phe Asp Pro Ile Leu Ala Ser Ser Gly Ile Asp Tyr Asp
    770                 775                 780

Ile Lys Ile Trp Ser Pro Leu Glu Glu Ser Arg Ile Phe Asn Arg Lys
785                 790                 795                 800

Leu Ala Asp Glu Val Ile Thr Arg Asn Glu Leu Met Leu Glu Glu Thr
                805                 810                 815

Arg Asn Thr Ile Thr Val Pro Ala Ser Phe Met Leu Arg Met Leu Ala
            820                 825                 830

Ser Leu Asn His Ile Arg Ala Asp Arg Leu Glu Gly Asp Arg Ser Glu
        835                 840                 845

Gly Ser Gly Gln Glu Asn Glu Asn Glu Asp Glu Glu
    850                 855                 860

<210> SEQ ID NO 3
<211> LENGTH: 3420
<212> TYPE: DNA
<213> ORGANISM: Homo sapiens
<220> FEATURE:
<221> NAME/KEY: CDS
<222> LOCATION: (176)..(2986)

<400> SEQUENCE: 3
cggccgggct tcaggggccc aggcgccgct gctgccaccg ccatctaacg ctgcgccctg      60
gaggcccggc gcgcggatgg tgccggtgcg gctcgggtgt tgaaacgggt gtccctccc      120 cctcctcccc tccccacgc ggtggtctcc cctcccaccc ggctcaggca gagcc atg      178
                                                           Met
                                                            1 tct cgg ggt ggc tcc tac cca cac ctg ttg tgg gac gtg agg aaa agg      226
Ser Arg Gly Gly Ser Tyr Pro His Leu Leu Trp Asp Val Arg Lys Arg
        5                   10                  15
```

| | | |
|---|---|---|
| ttc ctc ggg ctg gag gac ccg tcc cgg ctg cgg agt cgc tac ctg gga<br>Phe Leu Gly Leu Glu Asp Pro Ser Arg Leu Arg Ser Arg Tyr Leu Gly<br>20            25              30 | | 274 |
| aga aga gaa ttt atc caa aga tta aaa ctt gaa gca acc ctt aat gtg<br>Arg Arg Glu Phe Ile Gln Arg Leu Lys Leu Glu Ala Thr Leu Asn Val<br>35            40              45 | | 322 |
| cat gat ggt tgt gtt aat aca atc tgt tgg aat gac act gga gaa tat<br>His Asp Gly Cys Val Asn Thr Ile Cys Trp Asn Asp Thr Gly Glu Tyr<br>50            55              60                65 | | 370 |
| att tta tct ggc tca gat gac acc aaa tta gta att agt aat cct tac<br>Ile Leu Ser Gly Ser Asp Asp Thr Lys Leu Val Ile Ser Asn Pro Tyr<br>      70              75              80 | | 418 |
| agc aga aag gtt ttg aca aca att cgt tca ggg cac cga gca aac ata<br>Ser Arg Lys Val Leu Thr Thr Ile Arg Ser Gly His Arg Ala Asn Ile<br>            85              90              95 | | 466 |
| ttt agt gca aag ttc tta cct tgt aca aat gat aaa cag att gta tcc<br>Phe Ser Ala Lys Phe Leu Pro Cys Thr Asn Asp Lys Gln Ile Val Ser<br>            100             105             110 | | 514 |
| tgc tct gga gat gga gta ata ttt tat acc aac gtt gag caa gat gca<br>Cys Ser Gly Asp Gly Val Ile Phe Tyr Thr Asn Val Glu Gln Asp Ala<br>115            120             125 | | 562 |
| gaa acc aac aga caa tgc caa ttt acg tgt cat tat gga act act tat<br>Glu Thr Asn Arg Gln Cys Gln Phe Thr Cys His Tyr Gly Thr Thr Tyr<br>130            135             140             145 | | 610 |
| gag att atg act gta ccc aat gac cct tac act ttt ctc tct tgt ggt<br>Glu Ile Met Thr Val Pro Asn Asp Pro Tyr Thr Phe Leu Ser Cys Gly<br>            150             155             160 | | 658 |
| gaa gat gga act gtt agg tgg ttt gat aca cgc atc aaa act agc tgc<br>Glu Asp Gly Thr Val Arg Trp Phe Asp Thr Arg Ile Lys Thr Ser Cys<br>            165             170             175 | | 706 |
| aca aaa gaa gat tgt aaa gat gat att tta att aac tgt cga cgt gct<br>Thr Lys Glu Asp Cys Lys Asp Asp Ile Leu Ile Asn Cys Arg Arg Ala<br>            180             185             190 | | 754 |
| gcc acg tct gtt gct att tgc cca cca ata cca tat tac ctt gct gtt<br>Ala Thr Ser Val Ala Ile Cys Pro Pro Ile Pro Tyr Tyr Leu Ala Val<br>195            200             205 | | 802 |
| ggt tgt tct gac agc tca gta cga ata tat gat cgg cga atg ctg ggc<br>Gly Cys Ser Asp Ser Ser Val Arg Ile Tyr Asp Arg Arg Met Leu Gly<br>210            215             220             225 | | 850 |
| aca aga gct aca ggg aat tat gca ggt cga ggg act act gga atg gtt<br>Thr Arg Ala Thr Gly Asn Tyr Ala Gly Arg Gly Thr Thr Gly Met Val<br>            230             235             240 | | 898 |
| gcc cgt ttt att cct tcc cat ctt aat aat aag tcc tgc aga gtg aca<br>Ala Arg Phe Ile Pro Ser His Leu Asn Asn Lys Ser Cys Arg Val Thr<br>            245             250             255 | | 946 |
| tct ctg tgt tac agt gaa gat ggt caa gag att ctc gtt agt tac tct<br>Ser Leu Cys Tyr Ser Glu Asp Gly Gln Glu Ile Leu Val Ser Tyr Ser<br>            260             265             270 | | 994 |
| tca gat tac ata tat ctt ttt gac ccg aaa gat gat aca gca cga gaa<br>Ser Asp Tyr Ile Tyr Leu Phe Asp Pro Lys Asp Asp Thr Ala Arg Glu<br>275            280             285 | | 1042 |
| ctt aaa act cct tct gcg gaa gag aga aga gaa gag ttg cga caa cca<br>Leu Lys Thr Pro Ser Ala Glu Glu Arg Arg Glu Glu Leu Arg Gln Pro<br>290            295             300             305 | | 1090 |
| cca gtt aag cgt ttg aga ctt cgt ggt gat tgg tca gat act gga ccc<br>Pro Val Lys Arg Leu Arg Leu Arg Gly Asp Trp Ser Asp Thr Gly Pro<br>            310             315             320 | | 1138 |
| aga gca agg ccg gag agt gaa cga gaa cga gat gga gag cag agt ccc<br>Arg Ala Arg Pro Glu Ser Glu Arg Glu Arg Asp Gly Glu Gln Ser Pro<br>            325             330             335 | | 1186 |

-continued

```
aat gtg tca ttg atg cag aga atg tct gat atg tta tca aga tgg ttt     1234
Asn Val Ser Leu Met Gln Arg Met Ser Asp Met Leu Ser Arg Trp Phe
        340                 345                 350 gaa gaa gca agt gag gtt gca caa agc aat aga gga cga gga aga tct     1282
Glu Glu Ala Ser Glu Val Ala Gln Ser Asn Arg Gly Arg Gly Arg Ser
    355                 360                 365 cga ccc aga ggt gga aca agt caa tca gat att tca act ctt cct acg     1330
Arg Pro Arg Gly Gly Thr Ser Gln Ser Asp Ile Ser Thr Leu Pro Thr
370                 375                 380                 385 gtc cca tca agt cct gat ttg gaa gtg agt gaa act gca atg gaa gta     1378
Val Pro Ser Ser Pro Asp Leu Glu Val Ser Glu Thr Ala Met Glu Val
                390                 395                 400 gat act cca gct gaa caa ttt ctt cag cct tct aca tcc tct aca atg     1426
Asp Thr Pro Ala Glu Gln Phe Leu Gln Pro Ser Thr Ser Ser Thr Met
            405                 410                 415 tca gct cag gct cat tcg aca tca tct ccc aca gaa agc cct cat tct     1474
Ser Ala Gln Ala His Ser Thr Ser Ser Pro Thr Glu Ser Pro His Ser
        420                 425                 430 act cct ttg cta tct tct cca gat agt gaa caa agg cag tct gtt gag     1522
Thr Pro Leu Leu Ser Ser Pro Asp Ser Glu Gln Arg Gln Ser Val Glu
    435                 440                 445 gca tct gga cac cac aca cat cat cag tct gaa ttt tta agg ggg cct     1570
Ala Ser Gly His His Thr His His Gln Ser Glu Phe Leu Arg Gly Pro
450                 455                 460                 465 gag ata gct ttg ctt cgt aag cgc ctg caa caa ctg agg ctt aag aag     1618
Glu Ile Ala Leu Leu Arg Lys Arg Leu Gln Gln Leu Arg Leu Lys Lys
                470                 475                 480 gct gag cag cag agg cag caa gag cta gct gca cat acc cag caa cag     1666
Ala Glu Gln Gln Arg Gln Gln Glu Leu Ala Ala His Thr Gln Gln Gln
            485                 490                 495 cct tcc act tct gat cag tct tct cat gag ggc tct tca cag gac cct     1714
Pro Ser Thr Ser Asp Gln Ser Ser His Glu Gly Ser Ser Gln Asp Pro
        500                 505                 510 cat gct tca gat tct cct tct tct gtg gtt aac aaa cag ctc gga tcc     1762
His Ala Ser Asp Ser Pro Ser Ser Val Val Asn Lys Gln Leu Gly Ser
    515                 520                 525 atg tca ctt gac gag caa cag gat aac aat aat gaa aag ctg agc ccc     1810
Met Ser Leu Asp Glu Gln Gln Asp Asn Asn Asn Glu Lys Leu Ser Pro
530                 535                 540                 545 aaa cca ggg aca ggt gaa cca gtt tta agt ttg cac tac agc aca gaa     1858
Lys Pro Gly Thr Gly Glu Pro Val Leu Ser Leu His Tyr Ser Thr Glu
                550                 555                 560 gga aca act aca agc aca ata aaa ctg aac ttt aca gat gaa tgg agc     1906
Gly Thr Thr Thr Ser Thr Ile Lys Leu Asn Phe Thr Asp Glu Trp Ser
            565                 570                 575 agt ata gca tca agt tct aga gga att ggg agc cat tgc aaa tct gag     1954
Ser Ile Ala Ser Ser Ser Arg Gly Ile Gly Ser His Cys Lys Ser Glu
        580                 585                 590 ggt cag gag gaa tct ttc gtc cca cag agc tca gtg caa cca cca gaa     2002
Gly Gln Glu Glu Ser Phe Val Pro Gln Ser Ser Val Gln Pro Pro Glu
    595                 600                 605 gga gac agt gaa aca aaa gct cct gaa gaa tca tca gag gat gtg aca     2050
Gly Asp Ser Glu Thr Lys Ala Pro Glu Glu Ser Ser Glu Asp Val Thr
610                 615                 620                 625 aaa tat cag gaa gga gta tct gca gaa aac cca gtt gag aac cat atc     2098
Lys Tyr Gln Glu Gly Val Ser Ala Glu Asn Pro Val Glu Asn His Ile
                630                 635                 640 aat ata aca caa tca gat aag ttc aca gcc aag cca ttg gat tcc aac     2146
Asn Ile Thr Gln Ser Asp Lys Phe Thr Ala Lys Pro Leu Asp Ser Asn
```

```
                     645                 650                 655
tca gga gaa aga aat gac ctc aat ctt gat cgc tct tgt ggg gtt cca        2194
Ser Gly Glu Arg Asn Asp Leu Asn Leu Asp Arg Ser Cys Gly Val Pro
        660                 665                 670 gaa gaa tct gct tca tct gaa aaa gcc aag gaa cca gaa act tca gat        2242
Glu Glu Ser Ala Ser Ser Glu Lys Ala Lys Glu Pro Glu Thr Ser Asp
675                 680                 685 cag act agc act gag agt gct acc aat gaa aat aac acc aat cct gag        2290
Gln Thr Ser Thr Glu Ser Ala Thr Asn Glu Asn Asn Thr Asn Pro Glu
690                 695                 700                 705 cct cag ttc caa aca gaa gcc act ggg cct tca gct cat gaa gaa aca        2338
Pro Gln Phe Gln Thr Glu Ala Thr Gly Pro Ser Ala His Glu Glu Thr
            710                 715                 720 tcc acc agg gac tct gct ctt cag gac aca gat gac agt gat gat gac        2386
Ser Thr Arg Asp Ser Ala Leu Gln Asp Thr Asp Asp Ser Asp Asp Asp
                725                 730                 735 cca gtc ctg atc cca ggt gca agg tat cga gca gga cct ggt gat aga        2434
Pro Val Leu Ile Pro Gly Ala Arg Tyr Arg Ala Gly Pro Gly Asp Arg
                    740                 745                 750 cgc tct gct gtt gcc cgt att cag gag ttc ttc aga cgg aga aaa gaa        2482
Arg Ser Ala Val Ala Arg Ile Gln Glu Phe Phe Arg Arg Arg Lys Glu
                        755                 760                 765 agg aaa gaa atg gaa gaa ttg gat act ttg aac att aga agg ccg cta        2530
Arg Lys Glu Met Glu Glu Leu Asp Thr Leu Asn Ile Arg Arg Pro Leu
770                 775                 780                 785 gta aaa atg gtt tat aaa ggc cat cgc aac tcc agg aca atg ata aaa        2578
Val Lys Met Val Tyr Lys Gly His Arg Asn Ser Arg Thr Met Ile Lys
                790                 795                 800 gaa gcc aat ttc tgg ggt gct aac ttt gta atg act ggt tct gag tgt        2626
Glu Ala Asn Phe Trp Gly Ala Asn Phe Val Met Thr Gly Ser Glu Cys
                    805                 810                 815 ggc cac att ttc atc tgg gat cgg cac act gct gag cat ttg atg ctt        2674
Gly His Ile Phe Ile Trp Asp Arg His Thr Ala Glu His Leu Met Leu
                        820                 825                 830 ctg gaa gct gat aat cat gtg gta aac tgc ctg cag cca cat ccg ttt        2722
Leu Glu Ala Asp Asn His Val Val Asn Cys Leu Gln Pro His Pro Phe
835                 840                 845 gac cca att tta gcc tca tct ggc ata gat tat gac ata aag atc tgg        2770
Asp Pro Ile Leu Ala Ser Ser Gly Ile Asp Tyr Asp Ile Lys Ile Trp
850                 855                 860                 865 tca cca tta gaa gag tca agg att ttt aac cga aaa ctt gct gat gaa        2818
Ser Pro Leu Glu Glu Ser Arg Ile Phe Asn Arg Lys Leu Ala Asp Glu
                870                 875                 880 gtt ata act cga aac gaa ctc atg ctg gaa gaa act aga aac acc att        2866
Val Ile Thr Arg Asn Glu Leu Met Leu Glu Glu Thr Arg Asn Thr Ile
                    885                 890                 895 aca gtt cca gcc tct ttc atg ttg agg atg ttg gct tca ctt aat cat        2914
Thr Val Pro Ala Ser Phe Met Leu Arg Met Leu Ala Ser Leu Asn His
                        900                 905                 910 atc cga gct gac cgg ttg gag ggt gac aga tca gaa ggc tct ggt caa        2962
Ile Arg Ala Asp Arg Leu Glu Gly Asp Arg Ser Glu Gly Ser Gly Gln
915                 920                 925 gag aat gaa aat gag gat gag gaa taataaactc tttttggcaa gcacttaaat      3016
Glu Asn Glu Asn Glu Asp Glu Glu
930                 935 gttctgaaat tgtataaga catttattat ttttttttct ttacagagat ttagtgcaat      3076
tttaaggtta tggttttttgg agttttttccc tttttttggg ataacctaac attggtttgg  3136
aatgattgtg tgcatgaatt tgggagattg tataaaacaa aactagcaga atgtttttaa    3196
```

```
aacttttgc cgtgtatgag gagtgctaga aaatgcaaag tgcaatattt tccctaacct    3256
tcaaatgtgg gagcttggat caatgttgaa gaataatttt catcatagtg aaaatgttgg    3316
ttcaaataaa tttctacact tgccatttgc atgtttgttg ctttctaatt aaagaaactg    3376
gttgttttaa gatacccctga aaaaaaaaaa aaaaaaaaaa aaaa                   3420
```

<210> SEQ ID NO 4
<211> LENGTH: 937
<212> TYPE: PRT
<213> ORGANISM: Homo sapiens

<400> SEQUENCE: 4

```
Met Ser Arg Gly Gly Ser Tyr Pro His Leu Leu Trp Asp Val Arg Lys
 1               5                  10                  15

Arg Phe Leu Gly Leu Glu Asp Pro Ser Arg Leu Arg Ser Arg Tyr Leu
             20                  25                  30

Gly Arg Arg Glu Phe Ile Gln Arg Leu Lys Leu Glu Ala Thr Leu Asn
         35                  40                  45

Val His Asp Gly Cys Val Asn Thr Ile Cys Trp Asn Asp Thr Gly Glu
     50                  55                  60

Tyr Ile Leu Ser Gly Ser Asp Asp Thr Lys Leu Val Ile Ser Asn Pro
 65                  70                  75                  80

Tyr Ser Arg Lys Val Leu Thr Thr Ile Arg Ser Gly His Arg Ala Asn
                 85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Asn Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
                325                 330                 335
```

```
Pro Asn Val Ser Leu Met Gln Arg Met Ser Asp Met Leu Ser Arg Trp
            340                 345                 350

Phe Glu Glu Ala Ser Glu Val Ala Gln Ser Asn Arg Gly Arg Gly Arg
        355                 360                 365

Ser Arg Pro Arg Gly Gly Thr Ser Gln Ser Asp Ile Ser Thr Leu Pro
    370                 375                 380

Thr Val Pro Ser Ser Pro Asp Leu Glu Val Ser Glu Thr Ala Met Glu
385                 390                 395                 400

Val Asp Thr Pro Ala Glu Gln Phe Leu Gln Pro Ser Thr Ser Ser Thr
                405                 410                 415

Met Ser Ala Gln Ala His Ser Thr Ser Ser Pro Thr Glu Ser Pro His
            420                 425                 430

Ser Thr Pro Leu Leu Ser Ser Pro Asp Ser Glu Gln Arg Gln Ser Val
        435                 440                 445

Glu Ala Ser Gly His His Thr His His Gln Ser Glu Phe Leu Arg Gly
    450                 455                 460

Pro Glu Ile Ala Leu Leu Arg Lys Arg Leu Gln Gln Leu Arg Leu Lys
465                 470                 475                 480

Lys Ala Glu Gln Gln Arg Gln Gln Glu Leu Ala Ala His Thr Gln Gln
                485                 490                 495

Gln Pro Ser Thr Ser Asp Gln Ser Ser His Glu Gly Ser Ser Gln Asp
            500                 505                 510

Pro His Ala Ser Asp Ser Pro Ser Ser Val Val Asn Lys Gln Leu Gly
        515                 520                 525

Ser Met Ser Leu Asp Glu Gln Gln Asp Asn Asn Asn Glu Lys Leu Ser
    530                 535                 540

Pro Lys Pro Gly Thr Gly Glu Pro Val Leu Ser Leu His Tyr Ser Thr
545                 550                 555                 560

Glu Gly Thr Thr Thr Ser Thr Ile Lys Leu Asn Phe Thr Asp Glu Trp
                565                 570                 575

Ser Ser Ile Ala Ser Ser Arg Gly Ile Gly Ser His Cys Lys Ser
            580                 585                 590

Glu Gly Gln Glu Glu Ser Phe Val Pro Gln Ser Ser Val Gln Pro Pro
        595                 600                 605

Glu Gly Asp Ser Glu Thr Lys Ala Pro Glu Glu Ser Glu Asp Val
    610                 615                 620

Thr Lys Tyr Gln Glu Gly Val Ser Ala Glu Asn Pro Val Glu Asn His
625                 630                 635                 640

Ile Asn Ile Thr Gln Ser Asp Lys Phe Thr Ala Lys Pro Leu Asp Ser
                645                 650                 655

Asn Ser Gly Glu Arg Asn Asp Leu Asn Leu Asp Arg Ser Cys Gly Val
            660                 665                 670

Pro Glu Glu Ser Ala Ser Ser Glu Lys Ala Lys Glu Pro Glu Thr Ser
        675                 680                 685

Asp Gln Thr Ser Thr Glu Ser Ala Thr Asn Glu Asn Asn Thr Asn Pro
    690                 695                 700

Glu Pro Gln Phe Gln Thr Glu Ala Thr Gly Pro Ser Ala His Glu Glu
705                 710                 715                 720

Thr Ser Thr Arg Asp Ser Ala Leu Gln Asp Thr Asp Asp Ser Asp Asp
                725                 730                 735

Asp Pro Val Leu Ile Pro Gly Ala Arg Tyr Arg Ala Gly Pro Gly Asp
            740                 745                 750
```

-continued

```
Arg Arg Ser Ala Val Ala Arg Ile Gln Glu Phe Phe Arg Arg Lys
        755                 760                 765
Glu Arg Lys Glu Met Glu Glu Leu Asp Thr Leu Asn Ile Arg Arg Pro
    770                 775                 780
Leu Val Lys Met Val Tyr Lys Gly His Arg Asn Ser Arg Thr Met Ile
785                 790                 795                 800
Lys Glu Ala Asn Phe Trp Gly Ala Asn Phe Val Met Thr Gly Ser Glu
                805                 810                 815
Cys Gly His Ile Phe Ile Trp Asp Arg His Thr Ala Glu His Leu Met
            820                 825                 830
Leu Leu Glu Ala Asp Asn His Val Val Asn Cys Leu Gln Pro His Pro
        835                 840                 845
Phe Asp Pro Ile Leu Ala Ser Ser Gly Ile Asp Tyr Asp Ile Lys Ile
    850                 855                 860
Trp Ser Pro Leu Glu Glu Ser Arg Ile Phe Asn Arg Lys Leu Ala Asp
865                 870                 875                 880
Glu Val Ile Thr Arg Asn Glu Leu Met Leu Glu Thr Arg Asn Thr
                885                 890                 895
Ile Thr Val Pro Ala Ser Phe Met Leu Arg Met Leu Ala Ser Leu Asn
            900                 905                 910
His Ile Arg Ala Asp Arg Leu Glu Gly Asp Arg Ser Glu Gly Ser Gly
        915                 920                 925
Gln Glu Asn Glu Asn Glu Asp Glu Glu
    930                 935
```

<210> SEQ ID NO 5
<211> LENGTH: 21
<212> TYPE: DNA
<213> ORGANISM: Homo sapiens

<400> SEQUENCE: 5
caggacacag atgacagtga t                                    21

<210> SEQ ID NO 6
<211> LENGTH: 20
<212> TYPE: DNA
<213> ORGANISM: Homo sapiens

<400> SEQUENCE: 6
agagccttct gatctgtcac                                      20

<210> SEQ ID NO 7
<211> LENGTH: 9
<212> TYPE: PRT
<213> ORGANISM: Homo sapiens

<400> SEQUENCE: 7

Lys Thr Pro Ser Ala Glu Glu Arg
  1               5

<210> SEQ ID NO 8
<211> LENGTH: 8
<212> TYPE: PRT
<213> ORGANISM: Homo sapiens

<400> SEQUENCE: 8

Arg Ala Arg Pro Glu Ser Glu Arg
  1               5

```
<210> SEQ ID NO 9
<211> LENGTH: 7
<212> TYPE: PRT
<213> ORGANISM: Homo sapiens

<400> SEQUENCE: 9

Arg Met Ser Asp Met Ser Arg
 1               5

<210> SEQ ID NO 10
<211> LENGTH: 9
<212> TYPE: PRT
<213> ORGANISM: Homo sapiens

<400> SEQUENCE: 10

Asn Glu Lys Leu Ser Pro Lys Pro Gly
 1               5

<210> SEQ ID NO 11
<211> LENGTH: 35
<212> TYPE: PRT
<213> ORGANISM: Homo sapiens

<400> SEQUENCE: 11

Pro Asn Val Ser Leu Met Gln Arg Met Ser Asp Met Leu Ser Arg Trp
 1               5                   10                  15

Phe Glu Glu Ala Ser Glu Val Ala Gln Ser Asn Arg Gly Arg Gly Arg
             20                  25                  30

Ser Arg Pro
         35

<210> SEQ ID NO 12
<211> LENGTH: 25
<212> TYPE: PRT
<213> ORGANISM: Homo sapiens

<400> SEQUENCE: 12

Val Pro Ser Ser Pro Asp Leu Glu Val Ser Glu Thr Ala Met Glu Val
 1               5                   10                  15

Asp Thr Pro Ala Glu Gln Phe Leu Gln
             20                  25

<210> SEQ ID NO 13
<211> LENGTH: 25
<212> TYPE: PRT
<213> ORGANISM: Homo sapiens

<400> SEQUENCE: 13

Pro Val Leu Ser Leu His Tyr Ser Thr Glu Gly Thr Thr Thr Ser Thr
 1               5                   10                  15

Ile Lys Leu Asn Phe Thr Asp Glu Trp
             20                  25

<210> SEQ ID NO 14
<211> LENGTH: 24
<212> TYPE: PRT
<213> ORGANISM: Homo sapiens

<400> SEQUENCE: 14

Glu Thr Lys Ala Pro Glu Glu Ser Ser Glu Asp Val Thr Lys Tyr Gln
 1               5                   10                  15

Glu Gly Val Ser Ala Glu Asn Pro
             20
```

<210> SEQ ID NO 15
<211> LENGTH: 25
<212> TYPE: PRT
<213> ORGANISM: Homo sapiens

<400> SEQUENCE: 15

Glu Asn His Ile Asn Ile Thr Gln Ser Asp Lys Phe Thr Ala Lys Pro
1               5                   10                  15

Leu Asp Ser Asn Ser Gly Glu Arg Asn
            20                  25

<210> SEQ ID NO 16
<211> LENGTH: 24
<212> TYPE: PRT
<213> ORGANISM: Homo sapiens

<400> SEQUENCE: 16

Asn Thr Asn Pro Glu Pro Gln Phe Gln Thr Glu Ala Thr Gly Pro Ser
1               5                   10                  15

Ala His Glu Glu Thr Ser Thr Arg
            20

<210> SEQ ID NO 17
<211> LENGTH: 60
<212> TYPE: PRT
<213> ORGANISM: Homo sapiens

<400> SEQUENCE: 17

Asp Arg Arg Ser Ala Val Ala Arg Ile Gln Glu Phe Phe Arg Arg Arg
1               5                   10                  15

Lys Glu Arg Lys Glu Met Glu Glu Leu Asp Thr Leu Asn Ile Arg Arg
            20                  25                  30

Pro Leu Val Lys Met Val Tyr Lys Gly His Arg Asn Ser Arg Thr Met
        35                  40                  45

Ile Lys Glu Ala Asn Phe Trp Gly Ala Asn Phe Val
    50                  55                  60

<210> SEQ ID NO 18
<211> LENGTH: 37
<212> TYPE: PRT
<213> ORGANISM: Homo sapiens

<400> SEQUENCE: 18

Glu Cys Gly His Ile Phe Ile Trp Asp Arg His Thr Ala Glu His Leu
1               5                   10                  15

Met Leu Leu Glu Ala Asp Asn His Val Val Asn Cys Leu Gln Pro His
            20                  25                  30

Pro Phe Asp Pro Ile
        35

<210> SEQ ID NO 19
<211> LENGTH: 60
<212> TYPE: PRT
<213> ORGANISM: Homo sapiens

<400> SEQUENCE: 19

Leu Ala Ser Ser Gly Ile Asp Tyr Asp Ile Lys Ile Trp Ser Pro Leu
1               5                   10                  15

Glu Glu Ser Arg Ile Phe Asn Arg Lys Leu Ala Asp Glu Val Ile Thr
            20                  25                  30

```
Arg Asn Glu Leu Met Leu Glu Glu Thr Arg Asn Thr Ile Thr Val Pro
        35                  40                  45

Ala Ser Phe Met Leu Arg Met Leu Ala Ser Leu Asn
    50                  55                  60

<210> SEQ ID NO 20
<211> LENGTH: 11
<212> TYPE: PRT
<213> ORGANISM: Homo sapiens

<400> SEQUENCE: 20

Ser Gly Gln Glu Asn Glu Asn Glu Asp Glu Glu
1               5                   10
```